US009880161B2

(12) United States Patent
Horii et al.

(10) Patent No.: US 9,880,161 B2
(45) Date of Patent: Jan. 30, 2018

(54) DEVICE AND METHOD FOR ANALYZING STREPTAVIDIN

(71) Applicants: Katsunori Horii, Tokyo (JP); Naoto Kaneko, Tokyo (JP); Jou Akitomi, Tokyo (JP); Shintaro Kato, Tokyo (JP); Iwao Waga, Tokyo (JP)

(72) Inventors: Katsunori Horii, Tokyo (JP); Naoto Kaneko, Tokyo (JP); Jou Akitomi, Tokyo (JP); Shintaro Kato, Tokyo (JP); Iwao Waga, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 377 days.

(21) Appl. No.: 14/387,431

(22) PCT Filed: Mar. 21, 2013

(86) PCT No.: PCT/JP2013/058042
§ 371 (c)(1),
(2) Date: Sep. 23, 2014

(87) PCT Pub. No.: WO2013/141291
PCT Pub. Date: Sep. 26, 2013

(65) Prior Publication Data
US 2015/0086980 A1     Mar. 26, 2015

(30) Foreign Application Priority Data
Mar. 23, 2012  (JP) ................................ 2012-067947

(51) Int. Cl.
| *C12Q 1/68* | (2006.01) |
| *C07H 21/00* | (2006.01) |
| *G01N 33/50* | (2006.01) |
| *C12N 15/115* | (2010.01) |
| *G01N 33/543* | (2006.01) |
| *G01N 33/542* | (2006.01) |
| *G01N 33/68* | (2006.01) |
| *C12N 9/08* | (2006.01) |
| *C12N 15/113* | (2010.01) |
| *G01N 33/58* | (2006.01) |

(52) U.S. Cl.
CPC ..... *G01N 33/54306* (2013.01); *C12N 9/0065* (2013.01); *C12N 15/113* (2013.01); *C12N 15/115* (2013.01); *C12Y 111/01007* (2013.01); *G01N 33/542* (2013.01); *G01N 33/58* (2013.01); *G01N 33/68* (2013.01); *G01N 2333/36* (2013.01)

(58) Field of Classification Search
CPC ..... C12N 15/11; C12N 15/113; C12N 15/115; C07H 21/00; C12Q 1/6825
See application file for complete search history.

(56) References Cited

U.S. PATENT DOCUMENTS

| 5,424,186 A | 6/1995 | Fodor et al. |
| 5,807,522 A | 9/1998 | Brown et al. |
| 6,110,426 A | 8/2000 | Shalon et al. |
| 6,242,246 B1 | 6/2001 | Gold et al. |
| 2003/0027180 A1* | 2/2003 | Liu ............... C12N 15/1027 435/6.12 |
| 2005/0260655 A1 | 11/2005 | Liu et al. |
| 2008/0254446 A1 | 10/2008 | Sode et al. |

(Continued)

FOREIGN PATENT DOCUMENTS

| JP | 10-503841 | 4/1998 |
| JP | 2002-508191 | 3/2002 |

(Continued)

OTHER PUBLICATIONS

Chang et al., Amplified surface plasmon resonance immunosensor for interferon-Gamma based on a streptavidin-incorporated aptamer. Biosensors and Bioelectronics 37: 68 (2012).*
Hong et al., Applications of Aptasensors in Clinical Diagnostics. Sensors 12 : 1181 (2012).*
Schutze et al., Probing the SELEX Process with Next-Generation Sequencing. PLoS One 6 (12) : e29604 (2011).*
Willner et al., DNAzymes for sensing, nanobiotechnology and logic gate applications. Chemical Society Reviews 37 :1153 (2008).*
Zayats et al., Label-Free and Reagentless Aptamer-Based Sensors for Small Molecules. JACS 128 :13,666 (2006).*
Karp, Peter D., Genome Biology5:401(2004).*
X. Cheng et al., "General Peroxidase Activity of G-Quadruplex-Hemin Complexes and Its Application in Ligand Screening", Biochemistry, vol. 48, No. 33, pp. 7817-7823, 2009 with its Supporting Information.

(Continued)

Primary Examiner — Ethan C Whisenant
(74) Attorney, Agent, or Firm — Finnegan, Henderson, Farabow, Garrett & Dunner, L.L.P.

(57) ABSTRACT

The present invention provides a novel sensor for detecting streptavidin (SA). The nucleic acid sensor for analyzing SA of the present invention includes the following nucleic acid element that includes a catalyst nucleic acid molecule (D) that exerts a catalytic function and a binding nucleic acid molecule (A) that binds to SA. The nucleic acid element is a double-stranded nucleic acid element including a first strand and a second strand. The first strand (ss1) includes the binding nucleic acid molecule (A), a loop-forming sequence (L1), and the catalyst nucleic acid molecule (D) linked in this order. The second strand (ss2) includes a stem-forming sequence ($S_A$), a loop-forming sequence (L2), and a stem-forming sequence ($S_D$) linked in this order. In this nucleic acid element, in the absence of SA, the catalytic function of the catalyst nucleic acid molecule (D) is inhibited by stem formation in each of the stem-forming sequences ($S_A$) and ($S_D$), and in the presence of SA, the stem formation is released by a binding of the binding nucleic acid molecule (A) with the SA, and the catalytic function of the catalyst nucleic acid molecule (D) is exerted.

19 Claims, 6 Drawing Sheets

(56) References Cited

U.S. PATENT DOCUMENTS

| | | |
|---|---|---|
| 2010/0273240 A1 | 10/2010 | Sanyal |
| 2011/0045484 A1 | 2/2011 | Sode et al. |
| 2012/0202195 A1 | 8/2012 | Waga et al. |

FOREIGN PATENT DOCUMENTS

| | | |
|---|---|---|
| JP | 2009-296948 | 12/2009 |
| JP | 2010-130933 | 6/2010 |
| JP | 2010-207189 | 9/2010 |
| JP | 2011-503176 | 1/2011 |
| JP | 2011-155913 | 8/2011 |
| WO | WO 99/31275 A1 | 6/1999 |
| WO | WO 02/061078 A2 | 8/2002 |
| WO | WO 02/074978 A2 | 9/2002 |
| WO | WO 2005/049826 A1 | 6/2005 |
| WO | WO 2005/106035 A2 | 11/2005 |
| WO | WO 2009/063969 A1 | 5/2009 |
| WO | WO 2011/016565 A1 | 2/2011 |
| WO | WO 2012/002541 A1 | 1/2012 |

OTHER PUBLICATIONS

D. Li et al., "Amplified Analysis of Low-Molecular-Weight Substrates or Proteins by the Self-Assembly of DNAzyme-Aptamer Conjugates", J. Am. Chem. Soc., vol. 129, No. 18, pp. 5804-5805, 2007 with its Supporting Information.

F. Liu et al., "Highly Effective Colorimetric and Visual Detection of ATP by a DNAzyme-Aptamer Sensor", Chemistry & Biodiversity, vol. 8, No. 2, pp. 311-316, 2011.

G. Pelossof et al., "Amplified Biosensing Using the Horseradish Peroxidase-Mimicking DNAzyme as an Electrocatalyst", Analytical Chemistry, vol. 82, No. 11, pp. 4396-4402, 2010 with its Supporting Information.

Notification of Reason(s) for Rejection issued by the Japanese Patent Office dated Oct. 13, 2015, in counterpart Japanese Patent Application No. 2014-505954.

Japanese Office Action dated Apr. 20, 2016, by the Japanese Patent Office in counterpart Japanese Patent Application No. 2014-506266.

C. Teller et al., "Aptamer-DNAzyme Hairpins for Amplified Biosensing", Analytical Chemistry, vol. 81, No. 21, pp. 9114-9119, 2009.

P. Travascio et al., "DNA-enhanced peroxidase activity of a DNA aptamer-hemin complex", Chemistry & Biology, vol. 5, No. 9, pp. 505-517, 1998.

X. Cheng et al., "General Peroxidase Activity of G-Quadruplex-Hemin Complexes and Its Application in Ligand Screening", Biochemistry, vol. 48, No. 33, pp. 7817-7823, 2009.

T. Li et al., "Label-Free Colorimetric Detection of Aqueous Mercury Ion ($Hg^{2+}$) Using $Hg^{2+}$-Modulated G-Quadruplex-Based DNAzymes", Analytical Chemistry, vol. 81, No. 6, pp. 2144-2149, 2009.

M. Monsur et al., "Colorimetric Sensing by Using Allosteric-DNAzyme-Coupled Rolling Circle Amplification and a Peptide Nucleic Acid-Organic Dye Probe", Angewandte Chemie International Edition, vol. 48, pp. 3512-3515, 2009.

International Search Report dated May 21, 2013.

C. Srisawat et al., "Streptavidin aptamers: Affinity tags for the study of RNAs and ribonucleoproteins", RNA, Cold Spring Harbor Laboratory Press, vol. 7, No. 4, pp. 632-641, 2001.

Extended European Search Report dated Jan. 7, 2016, by the European Patent Office in counterpart European Patent Application No. 13763690.8.

* cited by examiner (A)

(B)

(A)

(B)

(A)

(B)

(A)

(B)

SEQUENCE LISTING

```
<160> NUMBER OF SEQ ID NOS: 80

<210> SEQ ID NO 1
<211> LENGTH: 85
<212> TYPE: DNA
<213> ORGANISM: Artificial
<220> FEATURE:
<223> OTHER INFORMATION: aptamer

<400> SEQUENCE: 1
```

```
taatacgact cactatagca atggtacggt acttcccgac gcaccgatcg caggttcggg    60
acaaaagtgc acgctacttt gctaa                                         85
```

<210> SEQ ID NO 2
<211> LENGTH: 18
<212> TYPE: DNA
<213> ORGANISM: Artificial
<220> FEATURE:
<223> OTHER INFORMATION: aptamer

<400> SEQUENCE: 2

```
acgcaccgat cgcaggtt                                                 18
```

<210> SEQ ID NO 3
<211> LENGTH: 20
<212> TYPE: DNA
<213> ORGANISM: Artificial
<220> FEATURE:
<223> OTHER INFORMATION: aptamer

<400> SEQUENCE: 3

```
gacgcaccga tcgcaggttc                                               20
```

<210> SEQ ID NO 4
<211> LENGTH: 22
<212> TYPE: DNA
<213> ORGANISM: Artificial
<220> FEATURE:
<223> OTHER INFORMATION: aptamer

<400> SEQUENCE: 4

```
cgacgcaccg atcgcaggtt cg                                            22
```

<210> SEQ ID NO 5
<211> LENGTH: 24
<212> TYPE: DNA
<213> ORGANISM: Artificial
<220> FEATURE:
<223> OTHER INFORMATION: aptamer

<400> SEQUENCE: 5

```
ccgacgcacc gatcgcaggt tcgg                                          24
```

<210> SEQ ID NO 6
<211> LENGTH: 26
<212> TYPE: DNA
<213> ORGANISM: Artificial
<220> FEATURE:
<223> OTHER INFORMATION: aptamer

<400> SEQUENCE: 6

```
cccgacgcac cgatcgcagg ttcggg                                        26
```

<210> SEQ ID NO 7
<211> LENGTH: 28
<212> TYPE: DNA
<213> ORGANISM: Artificial
<220> FEATURE:
<223> OTHER INFORMATION: aptamer

<400> SEQUENCE: 7

```
tcccgacgca ccgatcgcag gttcggga                                      28
```

<210> SEQ ID NO 8
<211> LENGTH: 50

```
<212> TYPE: DNA
<213> ORGANISM: Artificial
<220> FEATURE:
<223> OTHER INFORMATION: aptamer

<400> SEQUENCE: 8
gcaatggtac ggtacttccc gacgcaccga tcgcaggttc gggacaaaag          50

<210> SEQ ID NO 9
<211> LENGTH: 50
<212> TYPE: DNA
<213> ORGANISM: Artificial
<220> FEATURE:
<223> OTHER INFORMATION: aptamer

<400> SEQUENCE: 9
ggtacttccc gacgcaccga tcgcaggttc gggacaaaag tgcacgctac          50

<210> SEQ ID NO 10
<211> LENGTH: 60
<212> TYPE: DNA
<213> ORGANISM: Artificial
<220> FEATURE:
<223> OTHER INFORMATION: aptamer

<400> SEQUENCE: 10
gcaatggtac ggtacttccc gacgcaccga tcgcaggttc gggacaaaag tgcacgctac    60

<210> SEQ ID NO 11
<211> LENGTH: 18
<212> TYPE: DNA
<213> ORGANISM: Artificial
<220> FEATURE:
<223> OTHER INFORMATION: DNAzyme

<400> SEQUENCE: 11
ctgggaggga gggaggga                                              18

<210> SEQ ID NO 12
<211> LENGTH: 22
<212> TYPE: DNA
<213> ORGANISM: Artificial
<220> FEATURE:
<223> OTHER INFORMATION: DNAzyme

<400> SEQUENCE: 12
tgagggtggg gagggtgggg aa                                         22

<210> SEQ ID NO 13
<211> LENGTH: 22
<212> TYPE: DNA
<213> ORGANISM: Artificial
<220> FEATURE:
<223> OTHER INFORMATION: DNAzyme

<400> SEQUENCE: 13
tgaggggagg gagggcgggg aa                                         22

<210> SEQ ID NO 14
<211> LENGTH: 22
<212> TYPE: DNA
<213> ORGANISM: Artificial
<220> FEATURE:
<223> OTHER INFORMATION: DNAzyme

<400> SEQUENCE: 14
```
tgaggggtgg gagggagggg aa                          22

<210> SEQ ID NO 15
<211> LENGTH: 22
<212> TYPE: DNA
<213> ORGANISM: Artificial
<220> FEATURE:
<223> OTHER INFORMATION: DNAzyme

<400> SEQUENCE: 15
tgaggggtgg gagggacggg aa                          22

<210> SEQ ID NO 16
<211> LENGTH: 22
<212> TYPE: DNA
<213> ORGANISM: Artificial
<220> FEATURE:
<223> OTHER INFORMATION: DNAzyme

<400> SEQUENCE: 16
tgaggggtgg gagggtgggg aa                          22

<210> SEQ ID NO 17
<211> LENGTH: 22
<212> TYPE: DNA
<213> ORGANISM: Artificial
<220> FEATURE:
<223> OTHER INFORMATION: DNAzyme

<400> SEQUENCE: 17
tgaggggtgg gagggtcggg aa                          22

<210> SEQ ID NO 18
<211> LENGTH: 16
<212> TYPE: DNA
<213> ORGANISM: Artificial
<220> FEATURE:
<223> OTHER INFORMATION: DNAzyme

<400> SEQUENCE: 18
gggtgggagg gtcggg                                 16

<210> SEQ ID NO 19
<211> LENGTH: 22
<212> TYPE: DNA
<213> ORGANISM: Artificial
<220> FEATURE:
<223> OTHER INFORMATION: DNAzyme

<400> SEQUENCE: 19
tgaggggtgg gaggggtggg aa                          22

<210> SEQ ID NO 20
<211> LENGTH: 22
<212> TYPE: DNA
<213> ORGANISM: Artificial
<220> FEATURE:
<223> OTHER INFORMATION: DNAzyme

<400> SEQUENCE: 20
tgaggggtgg gaggggcggg aa                          22

<210> SEQ ID NO 21
<211> LENGTH: 22
<212> TYPE: DNA
<213> ORGANISM: Artificial

```
<220> FEATURE:
<223> OTHER INFORMATION: DNAzyme

<400> SEQUENCE: 21
tgaggggtgg gtgggcaggg aa                                              22

<210> SEQ ID NO 22
<211> LENGTH: 22
<212> TYPE: DNA
<213> ORGANISM: Artificial
<220> FEATURE:
<223> OTHER INFORMATION: DNAzyme

<400> SEQUENCE: 22
tgaggggtgg gtgggccggg aa                                              22

<210> SEQ ID NO 23
<211> LENGTH: 22
<212> TYPE: DNA
<213> ORGANISM: Artificial
<220> FEATURE:
<223> OTHER INFORMATION: DNAzyme

<400> SEQUENCE: 23
tgaggggtgg gcgggagggg aa                                              22

<210> SEQ ID NO 24
<211> LENGTH: 22
<212> TYPE: DNA
<213> ORGANISM: Artificial
<220> FEATURE:
<223> OTHER INFORMATION: DNAzyme

<400> SEQUENCE: 24
tgaggggtgg gcgggtcggg aa                                              22

<210> SEQ ID NO 25
<211> LENGTH: 22
<212> TYPE: DNA
<213> ORGANISM: Artificial
<220> FEATURE:
<223> OTHER INFORMATION: DNAzyme

<400> SEQUENCE: 25
tgaggggcgg gagggatggg aa                                              22

<210> SEQ ID NO 26
<211> LENGTH: 22
<212> TYPE: DNA
<213> ORGANISM: Artificial
<220> FEATURE:
<223> OTHER INFORMATION: DNAzyme

<400> SEQUENCE: 26
tgaggggcgg gagggtgggg aa                                              22

<210> SEQ ID NO 27
<211> LENGTH: 22
<212> TYPE: DNA
<213> ORGANISM: Artificial
<220> FEATURE:
<223> OTHER INFORMATION: DNAzyme

<400> SEQUENCE: 27
tgaggggcgg gagggtcggg aa                                              22
```

```
<210> SEQ ID NO 28
<211> LENGTH: 18
<212> TYPE: DNA
<213> ORGANISM: Artificial
<220> FEATURE:
<223> OTHER INFORMATION: DNAzyme

<400> SEQUENCE: 28
ctgggtgggc gggcggga                                              18

<210> SEQ ID NO 29
<211> LENGTH: 22
<212> TYPE: DNA
<213> ORGANISM: Artificial
<220> FEATURE:
<223> OTHER INFORMATION: DNAzyme

<400> SEQUENCE: 29
tgaggggagg gagggtcggg aa                                         22

<210> SEQ ID NO 30
<211> LENGTH: 22
<212> TYPE: DNA
<213> ORGANISM: Artificial
<220> FEATURE:
<223> OTHER INFORMATION: DNAzyme

<400> SEQUENCE: 30
tgaggggcgg gaggggtggg aa                                         22

<210> SEQ ID NO 31
<211> LENGTH: 15
<212> TYPE: DNA
<213> ORGANISM: Artificial
<220> FEATURE:
<223> OTHER INFORMATION: DNAzyme

<400> SEQUENCE: 31
gggcgggagg gaggg                                                 15

<210> SEQ ID NO 32
<211> LENGTH: 48
<212> TYPE: DNA
<213> ORGANISM: Artificial
<220> FEATURE:
<223> OTHER INFORMATION: nucleic acid sensor

<400> SEQUENCE: 32
ccgacgcacc gatcgcaggt tcggtttttt ttgggtggga gggtcggg             48

<210> SEQ ID NO 33
<211> LENGTH: 18
<212> TYPE: DNA
<213> ORGANISM: Artificial
<220> FEATURE:
<223> OTHER INFORMATION: nucleic acid sensor

<400> SEQUENCE: 33 caccctttttt tttccgaa                                             18

<210> SEQ ID NO 34
<211> LENGTH: 19
<212> TYPE: DNA
<213> ORGANISM: Artificial
<220> FEATURE:
<223> OTHER INFORMATION: nucleic acid sensor
```

```
<400> SEQUENCE: 34 caccctttttt tttccgaac                                              19

<210> SEQ ID NO 35
<211> LENGTH: 20
<212> TYPE: DNA
<213> ORGANISM: Artificial
<220> FEATURE:
<223> OTHER INFORMATION: nucleic acid sensor

<400> SEQUENCE: 35 caccctttttt tttccgaacc                                             20

<210> SEQ ID NO 36
<211> LENGTH: 21
<212> TYPE: DNA
<213> ORGANISM: Artificial
<220> FEATURE:
<223> OTHER INFORMATION: nucleic acid sensor

<400> SEQUENCE: 36 caccctttttt tttccgaacc t                                           21

<210> SEQ ID NO 37
<211> LENGTH: 19
<212> TYPE: DNA
<213> ORGANISM: Artificial
<220> FEATURE:
<223> OTHER INFORMATION: nucleic acid sensor

<400> SEQUENCE: 37 ccacccttttt ttttccgaa                                              19

<210> SEQ ID NO 38
<211> LENGTH: 20
<212> TYPE: DNA
<213> ORGANISM: Artificial
<220> FEATURE:
<223> OTHER INFORMATION: nucleic acid sensor

<400> SEQUENCE: 38 ccacccttttt ttttccgaac                                             20

<210> SEQ ID NO 39
<211> LENGTH: 21
<212> TYPE: DNA
<213> ORGANISM: Artificial
<220> FEATURE:
<223> OTHER INFORMATION: nucleic acid sensor

<400> SEQUENCE: 39 ccacccttttt ttttccgaac c                                           21

<210> SEQ ID NO 40
<211> LENGTH: 22
<212> TYPE: DNA
<213> ORGANISM: Artificial
<220> FEATURE:
<223> OTHER INFORMATION: nucleic acid sensor

<400> SEQUENCE: 40 ccacccttttt ttttccgaac ct                                          22

<210> SEQ ID NO 41
```

```
<211> LENGTH: 20
<212> TYPE: DNA
<213> ORGANISM: Artificial
<220> FEATURE:
<223> OTHER INFORMATION: nucleic acid sensor

<400> SEQUENCE: 41
cccacccttt tttttccgaa                                              20

<210> SEQ ID NO 42
<211> LENGTH: 21
<212> TYPE: DNA
<213> ORGANISM: Artificial
<220> FEATURE:
<223> OTHER INFORMATION: nucleic acid sensor

<400> SEQUENCE: 42
cccacccttt tttttccgaa c                                            21

<210> SEQ ID NO 43
<211> LENGTH: 22
<212> TYPE: DNA
<213> ORGANISM: Artificial
<220> FEATURE:
<223> OTHER INFORMATION: nucleic acid sensor

<400> SEQUENCE: 43
cccacccttt tttttccgaa cc                                           22

<210> SEQ ID NO 44
<211> LENGTH: 22
<212> TYPE: DNA
<213> ORGANISM: Artificial
<220> FEATURE:
<223> OTHER INFORMATION: nucleic acid sensor

<400> SEQUENCE: 44
cccacccttt tttttccgaa cc                                           22

<210> SEQ ID NO 45
<211> LENGTH: 21
<212> TYPE: DNA
<213> ORGANISM: Artificial
<220> FEATURE:
<223> OTHER INFORMATION: nucleic acid sensor

<400> SEQUENCE: 45
tcccaccctt tttttttccga a                                           21

<210> SEQ ID NO 46
<211> LENGTH: 51
<212> TYPE: DNA
<213> ORGANISM: Artificial
<220> FEATURE:
<223> OTHER INFORMATION: nucleic acid sensor

<400> SEQUENCE: 46
ggtttgggtg ggagggtcgg gcccttttccg acgcaccgat cgcaggttcg g          51

<210> SEQ ID NO 47
<211> LENGTH: 52
<212> TYPE: DNA
<213> ORGANISM: Artificial
<220> FEATURE:
<223> OTHER INFORMATION: nucleic acid sensor

<400> SEQUENCE: 47
```

-continued cggtttgggt gggagggtcg ggccctttcc gacgcaccga tcgcaggttc gg    52

<210> SEQ ID NO 48
<211> LENGTH: 53
<212> TYPE: DNA
<213> ORGANISM: Artificial
<220> FEATURE:
<223> OTHER INFORMATION: nucleic acid sensor

<400> SEQUENCE: 48
tcggtttggg tgggagggtc gggccctttc cgacgcaccg atcgcaggtt cgg    53

<210> SEQ ID NO 49
<211> LENGTH: 54
<212> TYPE: DNA
<213> ORGANISM: Artificial
<220> FEATURE:
<223> OTHER INFORMATION: nucleic acid sensor

<400> SEQUENCE: 49
gtcggtttgg gtgggagggt cgggcccttt ccgacgcacc gatcgcaggt tcgg    54

<210> SEQ ID NO 50
<211> LENGTH: 52
<212> TYPE: DNA
<213> ORGANISM: Artificial
<220> FEATURE:
<223> OTHER INFORMATION: nucleic acid sensor

<400> SEQUENCE: 50
ggtttgggtg ggagggtcgg gacccttttcc gacgcaccga tcgcaggttc gg    52

<210> SEQ ID NO 51
<211> LENGTH: 53
<212> TYPE: DNA
<213> ORGANISM: Artificial
<220> FEATURE:
<223> OTHER INFORMATION: nucleic acid sensor

<400> SEQUENCE: 51
cggtttgggt gggagggtcg ggaccctttc cgacgcaccg atcgcaggtt cgg    53

<210> SEQ ID NO 52
<211> LENGTH: 54
<212> TYPE: DNA
<213> ORGANISM: Artificial
<220> FEATURE:
<223> OTHER INFORMATION: nucleic acid sensor

<400> SEQUENCE: 52
tcggtttggg tgggagggtc gggaccccttt ccgacgcacc gatcgcaggt tcgg    54

<210> SEQ ID NO 53
<211> LENGTH: 55
<212> TYPE: DNA
<213> ORGANISM: Artificial
<220> FEATURE:
<223> OTHER INFORMATION: nucleic acid sensor

<400> SEQUENCE: 53
gtcggtttgg gtgggagggt cgggaccctt tccgacgcac cgatcgcagg ttcgg    55

<210> SEQ ID NO 54
<211> LENGTH: 53
<212> TYPE: DNA

<213> ORGANISM: Artificial
<220> FEATURE:
<223> OTHER INFORMATION: nucleic acid sensor

<400> SEQUENCE: 54
ggtttgggtg ggagggtcgg gcacccttct cgacgcaccg atcgcaggtt cgg    53

<210> SEQ ID NO 55
<211> LENGTH: 54
<212> TYPE: DNA
<213> ORGANISM: Artificial
<220> FEATURE:
<223> OTHER INFORMATION: nucleic acid sensor

<400> SEQUENCE: 55
cggtttgggt gggagggtcg gcacccttt ccgacgcacc gatcgcaggt tcgg    54

<210> SEQ ID NO 56
<211> LENGTH: 55
<212> TYPE: DNA
<213> ORGANISM: Artificial
<220> FEATURE:
<223> OTHER INFORMATION: nucleic acid sensor

<400> SEQUENCE: 56
tcggtttggg tgggagggtc gggcaccctt tccgacgcac cgatcgcagg ttcgg    55

<210> SEQ ID NO 57
<211> LENGTH: 55
<212> TYPE: DNA
<213> ORGANISM: Artificial
<220> FEATURE:
<223> OTHER INFORMATION: nucleic acid sensor

<400> SEQUENCE: 57
tcggtttggg tgggagggtc gggcaccctt tccgacgcac cgatcgcagg ttcgg    55

<210> SEQ ID NO 58
<211> LENGTH: 54
<212> TYPE: DNA
<213> ORGANISM: Artificial
<220> FEATURE:
<223> OTHER INFORMATION: nucleic acid sensor

<400> SEQUENCE: 58
ggtttgggtg ggagggtcgg gccacccttt ccgacgcacc gatcgcaggt tcgg    54

<210> SEQ ID NO 59
<211> LENGTH: 48
<212> TYPE: DNA
<213> ORGANISM: Artificial
<220> FEATURE:
<223> OTHER INFORMATION: nucleic acid sensor

<400> SEQUENCE: 59
ctgggaggga gggagggatt ttttccgacg caccgatcgc aggttcgg    48

<210> SEQ ID NO 60
<211> LENGTH: 46
<212> TYPE: DNA
<213> ORGANISM: Artificial
<220> FEATURE:
<223> OTHER INFORMATION: nucleic acid sensor

<400> SEQUENCE: 60
gggtgggagg gtcgggtttt ttccgacgca ccgatcgcag gttcgg    46

<210> SEQ ID NO 61
<211> LENGTH: 24
<212> TYPE: DNA
<213> ORGANISM: Artificial
<220> FEATURE:
<223> OTHER INFORMATION: DNAzyme

<400> SEQUENCE: 61
gtgggtcatt gtgggtgggt gtgg                                          24

<210> SEQ ID NO 62
<211> LENGTH: 18
<212> TYPE: DNA
<213> ORGANISM: Artificial
<220> FEATURE:
<223> OTHER INFORMATION: DNAzyme

<400> SEQUENCE: 62
gtgggtaggg cgggttgg                                                 18

<210> SEQ ID NO 63
<211> LENGTH: 15
<212> TYPE: DNA
<213> ORGANISM: Artificial
<220> FEATURE:
<223> OTHER INFORMATION: DNAzyme

<400> SEQUENCE: 63
ggttggtgtg gttgg                                                    15

<210> SEQ ID NO 64
<211> LENGTH: 23
<212> TYPE: DNA
<213> ORGANISM: Artificial
<220> FEATURE:
<223> OTHER INFORMATION: DNAzyme

<400> SEQUENCE: 64
ggggttgggg tgtggggttg ggg                                           23

<210> SEQ ID NO 65
<211> LENGTH: 22
<212> TYPE: DNA
<213> ORGANISM: Artificial
<220> FEATURE:
<223> OTHER INFORMATION: DNAzyme

<400> SEQUENCE: 65
agggttaggg ttagggttag gg                                            22

<210> SEQ ID NO 66
<211> LENGTH: 28
<212> TYPE: DNA
<213> ORGANISM: Artificial
<220> FEATURE:
<223> OTHER INFORMATION: DNAzyme

<400> SEQUENCE: 66
ggggttttgg ggttttgggg ttttgggg                                      28

<210> SEQ ID NO 67
<211> LENGTH: 23
<212> TYPE: DNA
<213> ORGANISM: Artificial
<220> FEATURE:

```
<223> OTHER INFORMATION: DNAzyme

<400> SEQUENCE: 67
gggcgcggga ggaaggggc ggg                                           23

<210> SEQ ID NO 68
<211> LENGTH: 17
<212> TYPE: DNA
<213> ORGANISM: Artificial
<220> FEATURE:
<223> OTHER INFORMATION: DNAzyme

<400> SEQUENCE: 68
gtgggtaggg cggttgg                                                 17

<210> SEQ ID NO 69
<211> LENGTH: 18
<212> TYPE: DNA
<213> ORGANISM: Artificial
<220> FEATURE:
<223> OTHER INFORMATION: DNAzyme

<400> SEQUENCE: 69
cgaggtgggt gggtggga                                                18

<210> SEQ ID NO 70
<211> LENGTH: 18
<212> TYPE: DNA
<213> ORGANISM: Artificial
<220> FEATURE:
<223> OTHER INFORMATION: DNAzyme

<400> SEQUENCE: 70
ctgggtgggt gggtggga                                                18

<210> SEQ ID NO 71
<211> LENGTH: 18
<212> TYPE: DNA
<213> ORGANISM: Artificial
<220> FEATURE:
<223> OTHER INFORMATION: DNAzyme

<400> SEQUENCE: 71
ctgggaggga gggaggga                                                18

<210> SEQ ID NO 72
<211> LENGTH: 18
<212> TYPE: DNA
<213> ORGANISM: Artificial
<220> FEATURE:
<223> OTHER INFORMATION: DNAzyme

<400> SEQUENCE: 72
ctgggcgggc gggcggga                                                18

<210> SEQ ID NO 73
<211> LENGTH: 21
<212> TYPE: DNA
<213> ORGANISM: Artificial
<220> FEATURE:
<223> OTHER INFORMATION: DNAzyme

<400> SEQUENCE: 73
ctgggttggg ttgggttggg a                                            21
```

```
<210> SEQ ID NO 74
<211> LENGTH: 22
<212> TYPE: DNA
<213> ORGANISM: Artificial
<220> FEATURE:
<223> OTHER INFORMATION: DNAzyme

<400> SEQUENCE: 74
ctggggtggg gtggggtggg ga                                              22

<210> SEQ ID NO 75
<211> LENGTH: 18
<212> TYPE: DNA
<213> ORGANISM: Artificial
<220> FEATURE:
<223> OTHER INFORMATION: DNAzyme

<400> SEQUENCE: 75
gggcgggccg gggcggg                                                    18

<210> SEQ ID NO 76
<211> LENGTH: 22
<212> TYPE: DNA
<213> ORGANISM: Artificial
<220> FEATURE:
<223> OTHER INFORMATION: DNAzyme

<400> SEQUENCE: 76
tgagggtggg gagggtgggg aa                                              22

<210> SEQ ID NO 77
<211> LENGTH: 21
<212> TYPE: DNA
<213> ORGANISM: Artificial
<220> FEATURE:
<223> OTHER INFORMATION: DNAzyme

<400> SEQUENCE: 77
cgggcgggcg cgagggaggg g                                               21

<210> SEQ ID NO 78
<211> LENGTH: 19
<212> TYPE: DNA
<213> ORGANISM: Artificial
<220> FEATURE:
<223> OTHER INFORMATION: DNAzyme

<400> SEQUENCE: 78
gggagggaga gggggcggg                                                  19

<210> SEQ ID NO 79
<211> LENGTH: 17
<212> TYPE: DNA
<213> ORGANISM: Artificial
<220> FEATURE:
<223> OTHER INFORMATION: DNAzyme

<400> SEQUENCE: 79
gggcgggcgc gggcggg                                                    17
```

```
<210> SEQ ID NO 80
<211> LENGTH: 17
<212> TYPE: DNA
<213> ORGANISM: Artificial
<220> FEATURE:
<223> OTHER INFORMATION: DNAzyme

<400> SEQUENCE: 80
gggtagggcg ggttggg                                                  17
```

US 9,880,161 B2

DEVICE AND METHOD FOR ANALYZING STREPTAVIDIN

TECHNICAL FIELD

The present invention relates to a nucleic acid sensor, a device, and a method for analyzing streptavidin.

BACKGROUND ART

Streptavidin (hereinafter referred to as "SA") is used as a substance for researches and inspections in various fields such as clinical medical care, food, and environment for the reason of the characteristics of a strong binding ability to biotin, high stability, and the like, for example. For example, in a method for detecting a target, the target is indirectly detected and determined quantitatively by detecting SA utilizing a binding among the target, biotin, and the SA, for example.

As described above, detection of SA is utilized in various fields, and various techniques for detecting SA have been studied. In the studies, it is required to construct a sensor capable of performing a simple and efficient measurement from the viewpoint of the wide use of the detection of SA (Non-Patent Document 1).

PRIOR ART DOCUMENT

Non-Patent Document

Non-Patent Document 1: Carsten Teller et. al., Anal. Chem. 2009, 81, 9114-9119

SUMMARY OF INVENTION

Problem to be Solved by the Invention

Hence, the present invention is intended to provide a novel sensor for detecting SA.

Means for Solving Problem

A nucleic acid sensor for analyzing streptavidin of the present invention is a nucleic acid sensor for analyzing SA, including the following nucleic acid element (I), (II), (II'), or (III) that includes a catalyst nucleic acid molecule (D) that exerts a catalytic function and a binding nucleic acid molecule (A) that binds to SA, (I) a double-stranded nucleic acid element including a first strand and a second strand, the first strand (ss1) including the binding nucleic acid molecule (A), a loop-forming sequence (L1), and the catalyst nucleic acid molecule (D) linked in this order, the second strand (ss2) including a stem-forming sequence ($S_A$), a loop-forming sequence (L2), and a stem-forming sequence ($S_D$) linked in this order, wherein a terminal region of the binding nucleic acid molecule (A) in the first strand (ss1) on the loop-forming sequence (L1) side is complementary to the stem-forming sequence ($S_A$) in the second strand (ss2), a terminal region of the catalyst nucleic acid molecule (D) in the first strand (ss1) on the loop-forming sequence (L1) side is complementary to the stem-forming sequence ($S_D$) in the second strand (ss2), the loop-forming sequence (L1) in the first strand (ss1) is non-complementary to the loop-forming sequence (L2) in the second strand (ss2), and in the absence of SA, the catalytic function of the catalyst nucleic acid molecule (D) is inhibited by stem formation in each of the stem-forming sequences ($S_A$) and ($S_D$), and in the presence of SA, the stem formation in each of the stem-forming sequences ($S_A$) and ($S_D$) is released by a binding of the SA with the binding nucleic acid molecule (A), and the catalytic function of the catalyst nucleic acid molecule (D) is exerted, (II) a single-stranded nucleic acid element including the binding nucleic acid molecule (A), a loop-forming sequence (L1), a stem-forming sequence ($S_D$), the catalyst nucleic acid molecule (D), a loop-forming sequence (L2), and a stem-forming sequence ($S_A$) linked in this order, wherein a terminal region of the binding nucleic acid molecule (A) on the loop-forming sequence (L1) side is complementary to the stem-forming sequence ($S_A$), a terminal region of the catalyst nucleic acid molecule (D) on the loop-forming sequence (L2) side is complementary to the stem-forming sequence ($S_D$), the loop-forming sequence (L1) is non-complementary to the loop-forming sequence (L2), and in the absence of SA, the catalytic function of the catalyst nucleic acid molecule (D) is inhibited by stem formation in each of the stem-forming sequences ($S_A$) and ($S_D$), and in the presence of SA, the stem formation in each of the stem-forming sequences ($S_A$) and ($S_D$) is released by a binding of the SA with the binding nucleic acid molecule (A), and the catalytic function of the catalyst nucleic acid molecule (D) is exerted, (II') a single-stranded nucleic acid element including the catalyst nucleic acid molecule (D), a loop-forming sequence (L2), a stem-forming sequence ($S_A$), the binding nucleic acid molecule (A), a loop-forming sequence (L1), and a stem-forming sequence ($S_D$) linked in this order, wherein a terminal region of the catalyst nucleic acid molecule (D) on the loop-forming sequence (L2) side is complementary to the stem-forming sequence ($S_D$), a terminal region of the binding nucleic acid molecule (A) on the loop-forming sequence (L1) side is complementary to the stem-forming sequence ($S_A$), the loop-forming sequence (L1) is non-complementary to the loop-forming sequence (L2), and in the absence of SA, the catalytic function of the catalyst nucleic acid molecule (D) is inhibited by stem formation in each of the stem-forming sequences ($S_A$) and ($S_D$), and in the presence of SA, the stem formation in each of the stem-forming sequences ($S_A$) and ($S_D$) is released by a binding of the SA with the binding nucleic acid molecule (A), and the catalytic function of the catalyst nucleic acid molecule (D) is exerted, and (III) a single-stranded nucleic acid element including the catalyst nucleic acid molecule (D), an intervening sequence (I), and the binding nucleic acid molecule (A) linked in this order, wherein the intervening sequence (I) is non-complementary to the catalyst nucleic acid molecule (D) and the binding nucleic acid molecule (A), and in the absence of SA, the catalytic function of the catalyst nucleic acid molecule (D) is inhibited, and in the presence of SA, the catalytic function of the catalyst nucleic acid molecule (D) is exerted.

The device for analyzing streptavidin of the present invention (hereinafter merely referred to as the "analysis device of the present invention") is a device for analyzing SA, including a base material; a nucleic acid sensor; and a detection part, wherein the nucleic acid sensor and the detection part are arranged in the base material, the nucleic acid sensor is the nucleic acid sensor according to the present invention, and the detection part is a detection part that detects the catalytic function of the catalyst nucleic acid molecule (D) in the nucleic acid sensor.

The method for analyzing streptavidin of the present invention (hereinafter merely referred to as the "analysis method of the present invention") is a method for analyzing SA, including: a contact step of causing a sample containing SA to be in contact with the nucleic acid sensor according to the present invention; and a detection step of detecting the catalytic function of the catalyst nucleic acid molecule (D) in the nucleic acid sensor to detect SA in the sample.

The analysis method of the present invention is a method for analyzing SA, including a contact step of causing a sample containing SA to be in contact with the analysis device according to the present invention; and a detection step of detecting the catalytic function of the catalyst nucleic acid molecule (D) in the detection part of the analysis device to detect SA in the sample.

Effects of the Invention

According to the nucleic acid sensor of the present invention, the catalytic function of the catalyst nucleic acid molecule (D) can be switched ON/OFF by a binding/non-binding of the binding nucleic acid molecule (A) with SA. Therefore, the presence or absence of and the amount of SA can be easily detected by detecting the catalytic function of the catalyst nucleic acid molecule (D). Moreover, the analysis device of the present invention uses the nucleic acid sensor as mentioned above. Therefore, for example, the analysis device can be downsized and formed into a chip, and many specimens can be easily analyzed by the analysis device. Thus, it can be said that the present invention is a really useful technology for researches and inspections in various fields such as clinical medical care, food, and environment, for example. In the present invention, the concept of the "analysis" encompasses quantitative analysis, semi-quantitative analysis, and qualitative analysis, for example.

DESCRIPTION OF EMBODIMENTS

Figure 1:
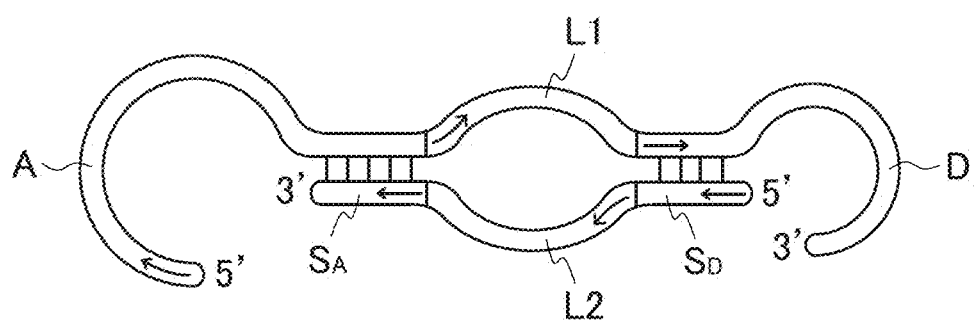
FIGS. 1A and 1B are schematic views showing an example of a nucleic acid element in the nucleic acid sensor of the present invention.
Figure 1:
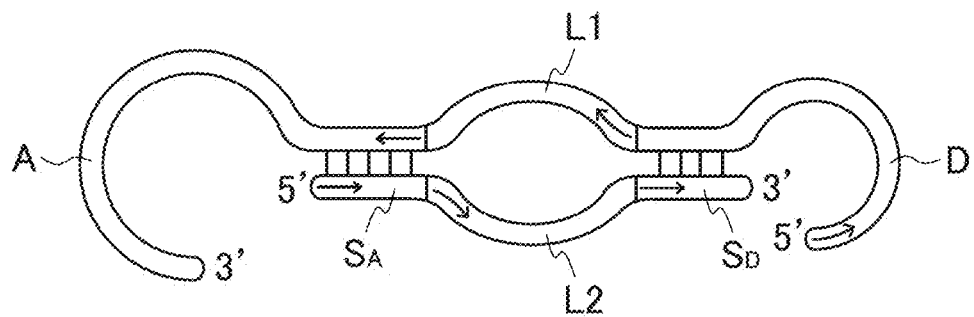

Nucleic Acid Sensor and Analysis Method Using the Same

The nucleic acid sensor for analyzing SA of the present invention includes, as mentioned above, the nucleic acid element (I), (II), (II'), or (III) that includes a catalytic nucleic acid molecule (D) that exerts a catalytic function and a binding nucleic acid molecule (A) that binds to SA.

The binding nucleic acid molecule (A) is not particularly limited as long as it is a nucleic acid molecule that binds to SA. In the present invention, "binding to SA" may encompass, for example, in addition to binding to SA, being bindable to a fragment of SA and being bindable to a derivative of SA.

The binding nucleic acid molecule (A) is, for example, a single strand. The length of the binding nucleic acid molecule (A) is not particularly limited. The lower limit thereof is, for example, 18-mer, preferably 20-mer, more preferably 24-mer, and the upper limit thereof is, for example, 120-mer, preferably 85-mer, more preferably 60-mer, yet more preferably 26-mer.

The binding nucleic acid molecule (A) can be, for example, a binding nucleic acid molecule that includes the following polynucleotide (a1), (a2), (a3), or (a4). The binding nucleic acid molecule (A) may be, for example, a molecule that is composed of or includes the polynucleotide. The binding nucleic acid molecule (A) including the following polynucleotide (a1), (a2), (a3), or (a4) can also be referred to as, for example, a binding DNA molecule.

(a1) a polynucleotide composed of a base sequence of any of SEQ ID NOs: 1 to 10,
(a2) a polynucleotide that is composed of a base sequence obtained by substitution, deletion, addition and/or insertion of at least one base in the base sequence of the polynucleotide (a1) and binds to SA,
(a3) a polynucleotide that is composed of a base sequence with 50% or more identity with the base sequence of the polynucleotide (a1) and is bindable to SA, and
(a4) a polynucleotide that is composed of a base sequence complementary to a base sequence that hybridizes to the base sequence of the polynucleotide (a1) under stringent conditions and is bindable to SA.

```
(85)
                                             SEQ ID NO: 1
taatacgact cactatagca atggtacggt acttcccgac
gcaccgatcg caggttcggg acaaaagtgc acgctacttt
gctaa

(18)
                                             SEQ ID NO: 2
AC GCACCGATCG CAGGTT

(20)
                                             SEQ ID NO: 3
GAC GCACCGATCG CAGGTTC

(22)
                                             SEQ ID NO: 4
CGAC GCACCGATCG CAGGTTCG

(24)
                                             SEQ ID NO: 5
CCGAC GCACCGATCG CAGGTTCGG

(26)
                                             SEQ ID NO: 6
CCCGAC GCACCGATCG CAGGTTCGGG

(28)
                                             SEQ ID NO: 7
TCCCGAC GCACCGATCG CAGGTTCGGG A (60_3-10)
                                             SEQ ID NO: 8
GCA ATGGTACGGT ACTTCCCGAC GCACCGATCG CAGGTTCGGG
ACAAAAG (60_5-10)
                                             SEQ ID NO: 9
GGT ACTTCCCGAC GCACCGATCG CAGGTTCGGG ACAAAAGTGC
ACGCTAC
```

-continued (60)

SEQ ID NO: 10
GCA ATGGTACGGT ACTTCCCGAC GCACCGATCG CAGGTTCGGG
ACAAAAGTGC ACGCTAC

In the polynucleotide (a2), "at least one" is not particularly limited as long as the polynucleotide (a2) binds to SA. The number of substituted bases is, in the base sequence of the polynucleotide (a1), for example, from 1 to 5, preferably from 1 to 4, more preferably from 1 to 3, yet more preferably 1 or 2, particularly preferably 1. The number of added or inserted bases is, in the base sequence of the polynucleotide (a1), for example, from 1 to 5, preferably from 1 to 4, more preferably from 1 to 3, yet more preferably 1 or 2, particularly preferably 1. The number of deleted bases is, in the base sequence of the polynucleotide (1a), for example, from 1 to 5, preferably from 1 to 4, more preferably from 1 to 3, yet more preferably 2 or 1, particularly preferably 1.

In the polynucleotide (a3), the identity is, to the base sequence of the polynucleotide (a1), for example, 70% or more, preferably 80% or more, more preferably 90% or more, yet more preferably 95% or more, 96% or more, 97% or more, 98% or more, particularly preferably 99% or more. The identity can be calculated using BLAST or the like under default conditions, for example.

In the polynucleotide (a4), "hybridization under stringent conditions" means hybridization under experimental conditions well known to those of ordinary skill in the art, for example. Specifically, the "stringent conditions" refer to conditions under which the base sequence can be identified after conducting hybridization at 60° C. to 68° C. in the presence of 0.7 to 1 mol/l NaCl and then washing at 65° C. to 68° C. using a 0.1- to 2-fold SSC solution, for example. Note here that 1×SSC is composed of 150 μmol/L NaCl and 15 μmol/L sodium citrate.

The binding nucleic acid molecule (A) is not limited by these examples as long as it is a nucleic acid molecule that binds to SA as mentioned above.

The binding nucleic acid molecule (A) is, for example, a molecule including a nucleotide residue and may be a molecule composed of only a nucleotide residue or a molecule including a nucleotide residue. Examples of the nucleotide include ribonucleotide, deoxyribonucleotide, and derivatives thereof. The binding nucleic acid molecule (A) may include, for example, only one kind of ribonucleotide, deoxyribonucleotide, and derivatives thereof, two or more kinds of them, or all of them. Specifically, the nucleic acid molecule may be DNA including deoxyribonucleotide and/or a derivative thereof, RNA including ribonucleotide and/or a derivative thereof, or chimera (DNA/RNA) including the former and the latter, for example.

The nucleotide may include, for example, either a natural base (non-artificial base) or a non-natural base (artificial base). Examples of the natural base include A, C, G, T, and U and modified bases thereof. Examples of the modification include methylation, fluorination, amination, and thiation. Examples of the non-natural base include 2'-fluoropyrimidine and 2'-O-methylpyrimidine, and specific examples thereof include 2'-fluorouracil, 2'-aminouracil, 2'-O-methyluracil, and 2-thiouracil. The nucleotide may be, for example, modified nucleotide, and examples of the modified nucleotide include 2'-methylated-uracil nucleotide residue, 2'-methylated-cytosine nucleotide residue, 2'-fluorinated-uracil nucleotide residue, 2'-fluorinated-cytosine nucleotide residue, 2'-aminated-uracil-nucleotide residue, 2'-aminated-cytosine nucleotide residue, 2'-thiated-uracil nucleotide residue, and 2'-thiated-cytosine nucleotide residue. The binding nucleic acid molecule (A) may include non-nucleotide such as PNA (peptide nucleic acid) or LNA (Locked Nucleic Acid), for example.

The catalyst nucleic acid molecule (D) is not limited as long as it exerts a catalytic function. The catalytic function is, for example, the catalytic function of an oxidation-reduction reaction. The oxidation-reduction reaction is not limited as long as it is a reaction in which electrons are transferred between two substrates in a course of generating a product from the substrates, for example. The kind of the oxidation-reduction reaction is not particularly limited. The catalytic function of the oxidation-reduction reaction can be, for example, activity which is the same as in enzyme and is, for example, specifically activity that is the same as in peroxidase (hereinafter referred to as "peroxidase-like activity"). The peroxidase activity can be, for example, horseradish peroxidase (HRP) activity. In the case where the catalyst nucleic acid molecule (D) is DNA such as described below, it can be called DNA enzyme or DNAzyme. In the case where the catalyst nucleic acid molecule (D) is RNA such as described below, it can be called RNA enzyme or RNAzyme.

The catalyst nucleic acid molecule (D) is preferably a nucleic acid that forms G-quartet (or G-tetrad), more preferably a nucleic acid that forms guanine quadruple (or G-quadruple). The G-tetrad is, for example, a plane structure of guanine tetramer, and the G-quadruplex is, for example, a structure in which plural G-tetrads are overlapped. The G-tetrad and the G-quadruplex are formed in a nucleic acid having a G-rich structural motif by repetition, for example. Examples of the G-tetrad include a parallel-type G-tetrad and an anti-parallel-type G-tetrad, and the G-tetrad is preferably a parallel-type G-tetrad. It is preferred that, in the nucleic acid element, stems are formed in the state where SA does not bind to the binding nucleic acid element (A), thereby inhibiting formation of G-tetrad in the catalyst nucleic acid molecule (D), and the formation of the stems is released by a binding of SA to the binding nucleic acid molecule (A), thereby forming G-tetrad in the catalyst nucleic acid molecule (D), for example.

The catalyst nucleic acid molecule (D) is preferably a nucleic acid capable of binding to porphyrin, specifically preferably a nucleic acid that forms G-tetrad and is capable of binding to porphyrin. It has been known that the nucleic acid having G-tetrad exerts the above-mentioned catalytic function of the oxidation-reduction reaction by forming a complex through binding of the nucleic acid with porphyrin, for example. It is preferred that, in the nucleic acid element, stems are formed in the state where SA does not bind to the binding nucleic acid molecule (A), thereby inhibiting a binding of the catalyst nucleic acid molecule (D) to porphyrin, and the formation of the stems are released by a binding of SA to the binding nucleic acid molecule (A), thereby binding the catalyst nucleic acid molecule (D) to porphyrin, for example. Specifically, it is preferred that, in the nucleic acid element, in the state where the binding nucleic acid molecule (A) does not bind to SA, formation of G-tetrad in the catalyst nucleic acid molecule (D) is inhibited, and a binding of the catalyst nucleic acid molecule (D) to porphyrin is inhibited, and by a binding of SA to the binding nucleic acid molecule (A), G-tetrad is formed in the catalyst nucleic acid molecule (D), and the catalyst nucleic acid molecule (D) binds to porphyrin, for example.

The porphyrin is not particularly limited, and examples thereof include unsubstituted porphyrin and a derivative thereof. Examples of the derivative include substituted porphyrin and a metal porphyrin obtained by forming a complex between porphyrin and a metal element. The substituted porphyrin can be, for example, N-methylmesoporphyrin. The metal porphyrin can be, for example, hemin that is a ferric complex. The porphyrin is, for example, preferably the metal porphyrin, more preferably hemin.

The catalyst nucleic acid molecule (D) is, for example, a single strand. The length of the catalyst nucleic acid molecule (D) is not particularly limited. The lower limit thereof is, for example, 11-mer, preferably 13-mer, more preferably 15-mer, and the upper limit thereof is, for example, 60-mer, preferably 36-mer, more preferably 18-mer.

Examples of the catalyst nucleic acid molecule (D) include DNAzymes disclosed in the following literatures (1) to (4) as DNAs having peroxidase activity.
(1) Travascio et. al., Chem. Biol., 1998, vol. 5, p. 505-517,
(2) Cheng et. al., Biochimistry, 2009, vol. 48, p. 7817-7823,
(3) Teller et. al., Anal. Chem., 2009, vol. 81, p. 9114-9119,
(4) Tao et. al., Anal. Chem., 2009, vol. 81, p. 2144-2149.

As a specific example of the catalyst nucleic acid molecule (D), there is a catalyst nucleic acid molecule including the following polynucleotide (d1), (d2), (d3), or (d4). The catalyst nucleic acid molecule (D) may be a molecule that is composed of or includes the polynucleotide. The catalyst nucleic acid molecule (D) including the polynucleotide (d1), (d2), (d3), or (d4) can also be referred to as a catalyst DNA molecule or DNAzyme, for example.
(d1) a polynucleotide composed of a base sequence of any of SEQ ID NOs: 11 to 31 and 61 to 80,
(d2) a polynucleotide that is composed of a base sequence obtained by substitution, deletion, addition, and/or insertion of at least one base in the base sequence of the polynucleotide (d1) and exerts a catalytic function of an oxidation-reduction reaction,
(d3) a polynucleotide that is composed of a base sequence with 50% or more identity with the base sequence of the polynucleotide (d1) and exerts a catalytic function of an oxidation-reduction reaction, and
(d4) a polynucleotide that is composed of a base sequence complementary to a base sequence that hybridizes to the base sequence of the polynucleotide (d1) under stringent conditions and exerts a catalytic function of an oxidation-reduction reaction.

```
EAD2
                                (SEQ ID NO: 11)
CTGGGAGGGAGGGAGGGA c-Myc
                                (SEQ ID NO: 12)
TGAGGGTGGGGAGGGTGGGGAA m_c-Myc-0527
                                (SEQ ID NO: 13)
TGAGGGGAGGGAGGGCGGGGAA m_c-Myc-0579
                                (SEQ ID NO: 14)
TGAGGGGTGGGAGGGAGGGAA m_c-Myc-0580
                                (SEQ ID NO: 15)
TGAGGGGTGGGAGGGACGGGAA m_c-Myc-0583
                                (SEQ ID NO: 16)
TGAGGGGTGGGAGGGTGGGAA m_c-Myc-0584
                                (SEQ ID NO: 17)
TGAGGGGTGGGAGGGTCGGGAA

-continued neco0584
                                (SEQ ID NO: 18)
GGGTGGGAGGGTCGGG m_c-Myc-0586
                                (SEQ ID NO: 19)
TGAGGGGTGGGAGGGGTGGGAA m_c-Myc-0588
                                (SEQ ID NO: 20)
TGAGGGGTGGGAGGGGCGGGAA m_c-Myc-0605
                                (SEQ ID NO: 21)
TGAGGGGTGGGTGGGCAGGGAA m_c-Myc-0608
                                (SEQ ID NO: 22)
TGAGGGGTGGGTGGGCCGGGAA m_c-Myc-0627
                                (SEQ ID NO: 23)
TGAGGGGTGGGCGGGAGGGGAA m_c-Myc-0632
                                (SEQ ID NO: 24)
TGAGGGGTGGGCGGGTCGGGAA m_c-Myc-0706
                                (SEQ ID NO: 25)
TGAGGGGCGGGAGGGATGGGAA m_c-Myc-0711
                                (SEQ ID NO: 26)
TGAGGGGCGGGAGGGTGGGGAA m_c-Myc-0712
                                (SEQ ID NO: 27)
TGAGGGGCGGGAGGGTCGGGAA m_EAD2-0032
                                (SEQ ID NO: 28)
CTGGGTGGGCGGGCGGGA m_c-Myc-0520
                                (SEQ ID NO: 29)
TGAGGGGAGGGAGGGTCGGGAA m_c-Myc-0714
                                (SEQ ID NO: 30)
TGAGGGGCGGGAGGGGTGGGAA m_TA-0420
                                (SEQ ID NO: 31)
GGGCGGGAGGGAGGG

SEQ ID NO: 61
GTGGGTCATTGTGGGTGGGTGTGG

SEQ ID NO: 62
GTGGGTAGGGCGGGTTGG

SEQ ID NO: 63
GGTTGGTGTGGTTGG

SEQ ID NO: 64
GGGGTTGGGGTGTGGGGTTGGGG

SEQ ID NO: 65
AGGGTTAGGGTTAGGGTTAGGG

SEQ ID NO: 66
GGGGTTTTGGGGTTTTGGGGTTTTGGGG

SEQ ID NO: 67
GGGCGCGGGAGGAAGGGGCGGG

SEQ ID NO: 68
GTGGGTAGGGCGGTTGG
```

-continued

CGAGGTGGGTGGGTGGGA    SEQ ID NO: 69

CTGGGTGGGTGGGTGGGA    SEQ ID NO: 70

CTGGGAGGGAGGGAGGGA    SEQ ID NO: 71

CTGGGCGGGCGGGCGGGA    SEQ ID NO: 72

CTGGGTTGGGTTGGGTTGGGA    SEQ ID NO: 73

CTGGGGTGGGGTGGGGTGGGGA    SEQ ID NO: 74

GGGCGGGCCGGGGCGGG    SEQ ID NO: 75

TGAGGGTGGGGAGGGTGGGGAA    SEQ ID NO: 76

CGGGCGGGCGCGAGGGAGGGG    SEQ ID NO: 77

GGGAGGGAGAGGGGGCGGG    SEQ ID NO: 78

GGGCGGGCGCGGGCGGG    SEQ ID NO: 79

GGGTAGGGCGGGTTGGG    SEQ ID NO: 80

In the polynucleotide (d2), "at least one" is not particularly limited as long as the polynucleotide (d2) exerts the catalytic function of the oxidation-reduction reaction. The number of substituted bases is, in the base sequence of the polynucleotide (d1), for example, from 1 to 5, preferably from 1 to 4, more preferably from 1 to 3, yet more preferably 1 or 2, particularly preferably 1. The number of added or inserted bases is, in the base sequence of the polynucleotide (d1), for example, from 1 to 5, preferably from 1 to 4, more preferably from 1 to 3, yet more preferably 1 or 2, particularly preferably 1. The number of deleted bases is, in the base sequence of the polynucleotide (d1), for example, from 1 to 5, preferably from 1 to 4, more preferably from 1 to 3, yet more preferably 2 or 1, particularly preferably 1.

In the polynucleotide (d3), the identity is, to the base sequence of the polynucleotide (d1), for example, 70% or more, preferably 80% or more, more preferably 90% or more, yet more preferably 95% or more, 96% or more, 97% or more, 98% or more, particularly preferably 99% or more. The identity can be calculated using BLAST or the like under default conditions, for example.

In the polynucleotide (d4), "hybridization under stringent conditions" is the same as mentioned above.

The catalyst nucleic acid molecule (D) is not limited by the examples of the polynucleotides (d1) to (d4) as long as it is a nucleic acid molecule that exerts the catalytic function as mentioned above.

The catalyst nucleic acid molecule (D) is, for example, a molecule including a nucleotide residue and may be a molecule composed of only or includes a nucleotide residue. The nucleotide is the same as mentioned above. The catalyst nucleic acid molecule (D) may include, for example, only one kind of ribonucleotide, deoxyribonucleotide, and derivatives thereof, two or more kinds of them, or all of them. Specifically, the nucleic acid molecule may be DNA including deoxyribonucleotide and/or a derivative thereof, RNA including ribonucleotide and/or a derivative thereof, or chimera (DNA/RNA) including the former and the latter, for example.

The nucleotide can be described with reference to examples shown for the binding nucleic acid molecule (A). The catalyst nucleic acid molecule (D) may include non-nucleotide such as PNA (peptide nucleic acid) or LNA (Locked Nucleic Acid), for example.

In the present invention, examples of the nucleic acid element include the above-mentioned nucleic acid elements (I), (II), (II'), and (III). Three forms of them are described below. Each form can be described with reference to the descriptions of the other forms unless otherwise shown.

As mentioned above, the nucleic acid element (I) is a double-stranded nucleic acid element composed of a first strand and a second strand. The second strand is also referred to as a block strand. The first strand (ss1) includes a binding nucleic acid molecule (A), a loop-forming sequence (L1), and a catalyst nucleic acid molecule (D) linked in this order. The second strand (ss2) includes a stem-forming sequence ($S_A$), a loop-forming sequence (L2), and a stem-forming sequence ($S_D$) linked in this order. A terminal region of the binding nucleic acid molecule (A) in the first strand (ss1) on the loop-forming sequence (L1) side is complementary to the stem-forming sequence ($S_A$) in the second strand (ss2). A terminal region of the catalyst nucleic acid molecule (D) in the first strand (ss1) on the loop-forming sequence (L1) side is complementary to the stem-forming sequence ($S_D$) in the second strand (ss2). The loop-forming sequence (L1) in the first strand (ss1) is non-complementary to the loop-forming sequence (L2) in the second strand (ss2). In the absence of SA, the catalytic function of the catalyst nucleic acid molecule (D) is inhibited by stem formation in each of the stem-forming sequences ($S_A$) and ($S_D$). The inhibition of the catalytic function occurs by caging the catalyst nucleic acid molecule through this stem formation. That is, by the stem formation, the catalyst nucleic acid molecule (D) cannot have a structure with which the catalytic function is exerted, thereby inhibiting the catalytic function. On the other hand, in the presence of SA, the stem formation in each of the stem-forming sequences ($S_A$) and ($S_D$) is released by a binding of the SA with the binding nucleic acid molecule (A), and the catalytic function of the catalyst nucleic acid molecule (D) is exerted. The exertion of the catalytic function occurs by releasing the stem formation and the caging of the catalyst nucleic acid molecule, for example. That is, by releasing the stem formation, the catalyst nucleic acid molecule (D) has an original structure with which the catalytic function is exerted, thereby exerting the catalytic function. Note here that the present invention is not limited by these mechanisms.

As described above, in the nucleic acid element (I), in the absence of SA, the catalytic function of the catalyst nucleic acid molecule (D) is inhibited (switched OFF) by the stem formation, and in the presence of SA, the catalytic function of the catalyst nucleic acid molecule (D) is exerted (switched ON) by releasing the stem formation. Specifically, in the nucleic acid element (I), for example, in the absence of SA, a terminal region of the binding nucleic acid molecule (A) in the first strand (ss1) on the loop-forming sequence (L1) side and the stem-forming sequence ($S_A$) in the second strand (ss2) form a stem, a terminal region of the catalyst nucleic acid molecule (D) in the first strand (ss1) on the loop-forming sequence (L1) side and the stem-forming sequence ($S_D$) in the second strand (ss2) form a stem, and the loop-forming sequences (L1) and (L2) form an internal loop between the two stems. In the present invention, "being complementary" may be, for example, the state where two regions aligned with each other are completely complementary to each other or the state where the two regions are complementary to each other to the extent that the two regions can form stems (hereinafter the same). Moreover, in the present invention, "being non-complementary" may be, for example, the state where two regions aligned with each other are completely non-complementary to each other or the state where the two regions are non-complementary to each other to the extent that the two regions can form an internal loop (hereinafter the same).

The schematic views of FIGS. 1A and 1B show the state of the nucleic acid element (I) in the absence of SA. The form shown in FIG. 1A and the form shown in FIG. 1B are reversed from each other in terms of the directions of the first strand (ss1) and the second strand (ss2). In FIGS. 1A and 1B, each arrow indicates the direction from the 5' side to the 3' side (hereinafter the same).

In each of FIGS. 1A and 1B, an upper strand is the first strand (ss1), A represents the binding nucleic acid molecule (A), L1 represents the loop-forming sequence (L1), and D represents the catalyst nucleic acid molecule (D). A lower strand is the second strand (ss2), $S_A$ represents the stem-forming sequence ($S_A$), L2 represents the loop-forming sequence (L2), and $S_D$ represents the stem-forming sequence ($S_D$). As shown in each of FIGS. 1A and 1B, in the absence of SA, two stems are formed at the respective two positions between the first strand (ss1) and the second strand (ss2), and an internal loop is formed between the stems. Specifically, a stem is formed between a terminal region of the binding nucleic acid molecule (A) on the loop-forming sequence (L1) side, a stem is formed between a terminal region of the catalyst nucleic acid molecule (D) on the loop-forming sequence (L1) side and the stem-forming sequence ($S_D$), and an internal loop is formed between the loop-forming sequences (L1) and (L2). In the presence of SA, the formation of the two stems is released by a binding of SA to the binding nucleic acid molecule (A), thereby exerting catalytic activity of the catalyst nucleic acid molecule (D).

The order of each component in the nucleic acid element (I) is not particularly limited. As shown in FIG. 1A, it is preferred that the first strand (ss1) includes, from the 5' side thereof, the binding nucleic acid molecule (A), the loop-forming sequence (L1), and the catalyst nucleic acid molecule (D) linked in this order, and the second strand (ss2) includes, from the 3' side thereof, the stem-forming sequence ($S_A$), the loop-forming sequence (L2), and the stem-forming sequence ($S_D$) linked in this order, for example. In this case, it is preferred that a 3' terminal region of the binding nucleic acid molecule (A) in the first strand (ss1) is complementary to the stem-forming sequence ($S_A$) in the second strand (ss2), and a 5' terminal region of the catalyst nucleic acid molecule (D) in the first strand (ss1) is complementary to the stem-forming sequence ($S_D$) in the second strand (ss2). As shown in FIG. 1B, for example, the first strand (ss1) may include, from the 3' side thereof, the binding nucleic acid molecule (A), the loop-forming sequence (L1), and the catalyst nucleic acid molecule (D) linked in this order, and the second strand (ss2) may include, from the 5' side thereof, the stem-forming sequence ($S_A$), the loop-forming sequence (L2), and the stem-forming sequence ($S_D$) linked in this order. In this case, it is preferred that a 5' terminal region of the binding nucleic acid molecule (A) in the first strand (ss1) is complementary to the stem-forming sequence ($S_A$) in the second strand (ss2), and a 3' terminal region of the catalyst nucleic acid molecule (D) in the first strand (ss1) is complementary to the stem-forming sequence ($S_D$) in the second strand (ss2). It is assumed that the nucleic acid element (I) can perform detection with superior sensitivity by forming an internal loop as described above. The present invention, however, is not limited by the assumption.

In the nucleic acid element (I), the length of the internal loop is not particularly limited. The length of each of the loop-forming sequence (L1) in the first strand (ss1) and the loop-forming sequence (L2) in the second strand (ss2) is, for example, from 0- to 30-mer, preferably from 1- to 30-mer, more preferably from 1- to 15-mer, yet more preferably from 1- to 6-mer. The lengths of the loop-forming sequences (L1) and (L2) may be identical to or different from each other, for example. In the latter case, the difference in length is not particularly limited and is, for example, from 1- to 10-mer, preferably 1- or 2-mer, more preferably 1-mer. The nucleic acid element (I) may include only either one of the loop-forming sequences (L1) and (L2). It is assumed that the nucleic acid element (I) can perform detection with superior sensitivity by forming an internal loop as described above. The present invention, however, is not limited by the assumption.

In the nucleic acid element (I), the length of each stem is not particularly limited. The length of the stem can be adjusted by the lengths of the stem-forming sequences ($S_A$) and ($S_D$) in the second strand (ss2), for example. The length of the stem-forming sequence ($S_A$) is, for example, from 0- to 60-mer, from 1- to 60-mer, preferably from 0- to 10-mer, from 1- to 10-mer. The length of the stem-forming sequence ($S_D$) is, for example, from 0- to 30-mer, from 1- to 30-mer, more preferably from 0- to 10-mer, from 1- to 10-mer, yet more preferably from 1- to 6-mer. The lengths of the stem-forming sequences ($S_A$) and ($S_D$) may be identical to each other, the former may be longer than the latter, or the latter may be longer than the former, for example.

In the nucleic acid element (I), the lengths of the first strand (ss1) and the second strand (ss2) are not particularly limited. The length of the first strand (ss1) is, for example, from 40- to 200-mer, preferably from 42- to 100-mer, more preferably from 45- to 60-mer. The length of the second strand (ss2) is, for example, from 4- to 120-mer, preferably from 5- to 25-mer, more preferably from 10- to 15-mer.

Specific examples of the nucleic acid element (I) are shown below. The present invention, however, is not limited thereby. Examples of the first strand (ss1) are shown below. In the following sequence, the underlined portion on the 5'-side indicates an SA aptamer (A in FIG. 1A) of SEQ ID NO: 5, the poly dT indicates the loop-forming sequence (L1 in FIG. 1A), and the underlined portion on the 3' side indicates DNAzyme (D in FIG. 1A) of SEQ ID NO: 18 (neco0584).

SA.neco.D3A2

(SEQ ID NO: 32)

5'-<u>CCGACGCACCGATCGCAGGTTCGG</u>TTTTTTTT<u>GGG</u>

<u>TGGGAGGGTCGGG</u>-3'

Examples of the second strand (ss2) to be paired with the first strand (ss1) are shown below. In each of the following sequences, the underlined portion on the 5' side indicates the stem-forming sequence ($S_D$ in FIG. 1A) complementary to a 5' side region of the DNAzyme in the first strand (ss1), the poly dT indicates the loop-forming sequence (L2 in FIG. 1A), and the underlined portion on the 3' side is the stem-forming sequence ($S_A$ in FIG. 1A) complementary to a 3' side region of the SA aptamer.

```
SA.neco.D5.A5
                                          (SEQ ID NO: 33)
5'-CACCCTTTTTTTCCGAA-3'

SA.neco.D5.A6
                                          (SEQ ID NO: 34)
5'-CACCCTTTTTTTCCGAAC-3'

SA.neco.D5.A7
                                          (SEQ ID NO: 35)
5'-CACCCTTTTTTTCCGAACC-3'

SA.neco.D5.A8
                                          (SEQ ID NO: 36)
5'-CACCCTTTTTTTCCGAACCT-3'

SA.neco.D6.A5
                                          (SEQ ID NO: 37)
5'-CCACCCTTTTTTTCCGAA-3'

SA.neco.D6.A6
                                          (SEQ ID NO: 38)
5'-CCACCCTTTTTTTCCGAAC-3'

SA.neco.D6.A7
                                          (SEQ ID NO: 39)
5'-CCACCCTTTTTTTCCGAACC-3'

SA.neco.D6.A8
                                          (SEQ ID NO: 40)
5'-CCACCCTTTTTTTCCGAACCT-3'

SA.neco.D7.A5
                                          (SEQ ID NO: 41)
5'-CCCACCCTTTTTTTCCGAA-3'

SA.neco.D7.A6
                                          (SEQ ID NO: 42)
5'-CCCACCCTTTTTTTCCGAAC-3'

SA.neco.D7.A7
                                          (SEQ ID NO: 43)
5'-CCCACCCTTTTTTTCCGAACC-3'

SA.neco.D7.A8
                                          (SEQ ID NO: 44)
5'-CCCACCCTTTTTTTCCGAACC-3'

SA.neco.D8.A5
                                          (SEQ ID NO: 45)
5'-TCCCACCCTTTTTTTCCGAA-3'
```

The nucleic acid element (II) is, as mentioned above, a single-stranded nucleic acid element and includes a binding nucleic acid molecule (A), a loop-forming sequence (L1), a stem-forming sequence ($S_D$), a catalyst nucleic acid molecule (D), a loop-forming sequence (L2), and a stem-forming sequence ($S_A$) linked in this order. A terminal region of the binding nucleic acid molecule (A) on the loop-forming sequence (L1) side is complementary to the stem-forming sequence ($S_A$), a terminal region of the catalyst nucleic acid molecule (D) on the loop-forming sequence (L2) side is complementary to the stem-forming sequence ($S_D$), and the loop-forming sequence (L1) is non-complementary to the loop-forming sequence (L2).

In the nucleic acid element (II), in the absence of SA, the catalytic function of the catalyst nucleic acid molecule (D) is inhibited by stem formation in each of the stem-forming sequences ($S_A$) and ($S_D$). The inhibition of the catalytic function occurs by caging the catalyst nucleic acid molecule through such stem formation caused by self-association. That is, by the stem formation, the catalyst nucleic acid molecule (D) cannot have an original structure with which the catalytic function is exerted, thereby inhibiting the catalytic function. On the other hand, in the presence of SA, the stem formation in each of the stem-forming sequences ($S_A$) and ($S_D$) is released by a binding of the SA with the binding nucleic acid molecule (A), and the catalytic function of the catalyst nucleic acid molecule (D) is exerted. The exertion of the catalytic function occurs by releasing the stem formation caused by the self-association and the caging of the catalyst nucleic acid molecule, for example. That is, by releasing the stem formation, the catalyst nucleic acid molecule (D) has an original structure with which the catalytic function is exerted, thereby exerting the catalytic function. Note here that the present invention is not limited by these mechanisms.

As described above, as in the nucleic acid element (I), in the nucleic acid element (II), in the absence of SA, the catalytic function of the catalyst nucleic acid molecule (D) is inhibited (switched OFF) by the stem formation, and in the presence of SA, the catalytic function of the catalyst nucleic acid molecule (D) is exerted (switched ON) by releasing the stem formation. Specifically, in the nucleic acid element (II), for example, in the absence of SA, a terminal region of the binding nucleic acid molecule (A) on the loop-forming sequence (L1) side and the stem-forming sequence ($S_A$) form a stem, a terminal region of the catalyst nucleic acid molecule (D) on the loop-forming sequence (L2) side and the stem-forming sequence ($S_D$) form a stem, and the loop-forming sequences (L1) and (L2) form an internal loop between the two stems.

Figure 2:
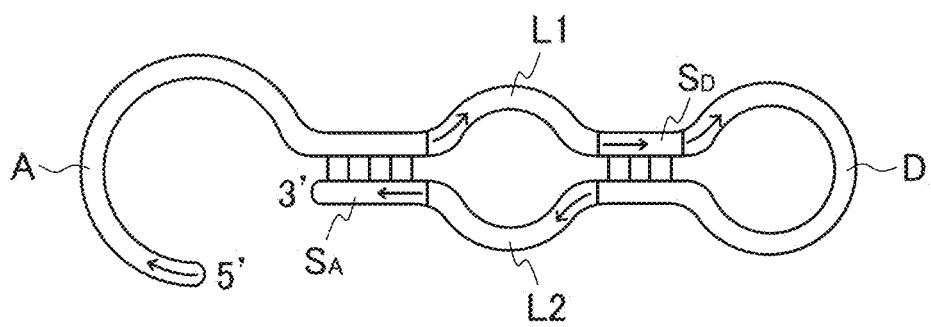
FIGS. 2A and 2B are schematic views showing another example of a nucleic acid element in the nucleic acid sensor of the present invention.
Figure 2:
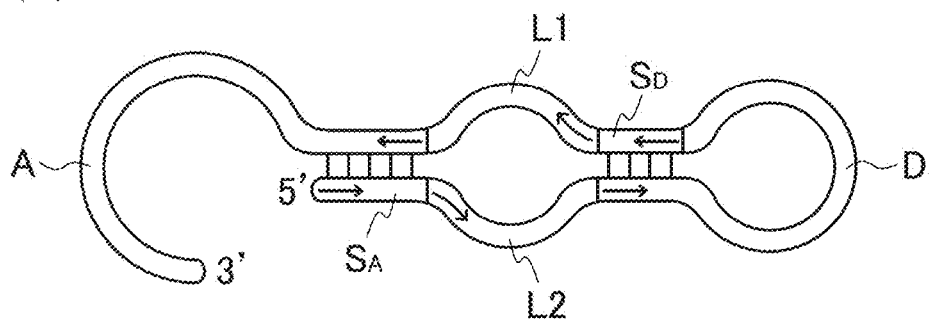

The schematic views of FIGS. 2A and 2B show the state of the nucleic acid element (II) in the absence of SA. The form shown in FIG. 2A and the form shown in FIG. 2B are reversed from each other in terms of the direction.

In each of FIGS. 2A and 2B, A represents the binding nucleic acid molecule (A), L1 represents the loop-forming sequence (L1), $S_D$ represents the stem-forming sequence ($S_D$), D represents the catalyst nucleic acid molecule (D), L2 represents the loop-forming sequence (L2), and $S_A$ represents the stem-forming sequence ($S_A$). As shown in each of FIGS. 2A and 2B, in the absence of SA, two stems are formed at the respective two positions by self-annealing of the nucleic acid element (II), and an internal loop is formed between the stems. Specifically, a stem is formed between a terminal region of the binding nucleic acid molecule (A) on the loop-forming sequence (L1) side, a stem is formed between a terminal region of the catalyst nucleic acid molecule (D) on the loop-forming sequence (L2) side and the stem-forming sequence ($S_D$), and an internal loop is formed between the loop-forming sequences (L1) and (L2). In the presence of SA, the formation of the two stems is released by a binding of SA to the binding nucleic acid molecule (A), thereby exerting catalytic activity of the catalyst nucleic acid molecule (D).

The order of each component in the nucleic acid element (II) is not particularly limited. As shown in FIG. 2B, it is preferred that the nucleic acid element (II) includes, from the 3' side thereof, the binding nucleic acid molecule (A), the loop-forming sequence (L1), the stem-forming sequence ($S_D$), the catalyst nucleic acid molecule (D), the loop-forming sequence (L2), and the stem-forming sequence ($S_A$) linked in this order, for example. In this case, it is preferred that a 5' terminal region of the binding nucleic acid molecule (A) is complementary to the stem-forming sequence ($S_A$), and a 5' terminal region of the catalyst nucleic acid molecule (D) is complementary to the stem-forming sequence ($S_D$). As shown in FIG. 2A, the nucleic acid element (II) may include, from the 5' side thereof, the binding nucleic acid molecule (A), the loop-forming sequence (L1), the stem-forming sequence ($S_D$), the catalyst nucleic acid molecule (D), the loop-forming sequence (L2), and the stem-forming sequence (S_A) linked in this order, for example. In this case, it is preferred that a 3' terminal region of the binding nucleic acid molecule (A) is complementary to the stem-forming sequence (S_A), and a 3' terminal region of the catalyst nucleic acid molecule (D) is complementary to the stem-forming sequence (S_D).

In the nucleic acid element (II), the length of the internal loop is not particularly limited. The length of each of the loop-forming sequences (L1) and (L2) is, for example, from 0- to 30-mer, preferably from 1- to 30-mer, more preferably from 1- to 15-mer, yet more preferably from 1- to 6-mer. The lengths of the loop-forming sequences (L1) and (L2) may be identical to or different from each other, for example. In the latter case, the difference in length is not particularly limited and is, for example, from 1- to 10-mer, preferably 1- or 2-mer, more preferably 1-mer. The nucleic acid element (II) may include only either one of the loop-forming sequences (L1) and (L2). It is assumed that the nucleic acid element (II) can perform detection with superior sensitivity by forming an internal loop as described above. The present invention, however, is not limited by the assumption.

In the nucleic acid element (II), the length of each stem is not particularly limited. The length of the stem can be adjusted by the lengths of the stem-forming sequences (S_A) and (S_D), for example. The length of the stem-forming sequence (S_A) is, for example, from 0- to 60-mer, from 1- to 60-mer, preferably from 1- to 10-mer, more preferably from 1- to 7-mer. The length of the stem-forming sequence (S_D) is, for example, from 0- to 30-mer, from 1- to 30-mer, preferably from 0- to 10-mer, from 1- to 10-mer, more preferably from 0- to 7-mer, from 1- to 7-mer. The lengths of the stem-forming sequences (S_A) and (S_D) may be identical to each other, the former may be longer than the latter, or the latter may be longer than the former, for example.

The length of the nucleic acid element (II) is not particularly limited and is, for example, from 40- to 120-mer, preferably from 45- to 100-mer, more preferably from 50- to 80-mer.

Specific examples of the nucleic acid element (II) are shown below. The present invention, however, is not limited thereby. In each of the following sequences, from the 5' side thereof, the sequence indicated by lower-case letters indicates the stem-forming sequence (S_A in FIG. 2B), the poly dT indicated by capital letters indicates the loop-forming sequence (L2 in FIG. 2B), the underlined portion indicates DNAzyme (D in FIG. 2B) of SEQ ID NO: 18 (neco0584), the sequence indicated by lower-case letters indicates the stem-forming sequence (S_D in FIG. 2B), the poly dT indicated by capital letters indicates the loop-forming sequence (L1 in FIG. 2B), and the underlined portion indicates an SA aptamer of SEQ ID NO: 5 (A in FIG. 2B).

SA.neco.D3A2
(SEQ ID NO: 46)
5'-ggTTTGGGTGGGAGGGTCGGGcccTTTCCGACGCACCGATCGCA
GGTTCGG-3'

SA.neco.D3A3
(SEQ ID NO: 47)
5'-cggTTTGGGTGGGAGGGTCGGGcccTTTCCGACGCACCGATCGC
AGGTTCGG-3'

SA.neco.D3A4
(SEQ ID NO: 48)
5'-tcggTTTGGGTGGGAGGGTCGGGcccTTTCCGACGCACCGATCG
CAGGTTCGG-3'

-continued

SA.neco.D3A5
(SEQ ID NO: 49)
5'-gtcggTTTGGGTGGGAGGGTCGGGcccTTTCCGACGCACCGATC
GCAGGTTCGG-3'

SA.neco.D4A2
(SEQ ID NO: 50)
5'-ggTTTGGGtGGGAGGGTCGGGacccTTTCCGACGCACCGATCGC
AGGTTCGG-3'

SA.neco.D4A3
(SEQ ID NO: 51)
5'-cggTTTGGGTGGGAGGGTCGGGacccTTTCCGACGCACCGATCG
CAGGTTCGG-3'

SA.neco.D4A4
(SEQ ID NO: 52)
5'-tcggTTTGGGTGGGAGGGTCGGGacccTTTCCGACGCACCGATC
GCAGGTTCGG-3'

SA.neco.D4A5
(SEQ ID NO: 53)
5'-gtcggTTTGGGTGGGAGGGTCGGGacccTTTCCGACGCACCGAT
CGCAGGTTCGG-3'

SA.neco.D5A2
(SEQ ID NO: 54)
5'-ggTTTGGGTGGGAGGGTCGGGcacccTTTCCGACGCACCGATCG
CAGGTTCGG-3'

SA.neco.D5A3
(SEQ ID NO: 55)
5'-cggTTTGGGTGGGAGGGTCGGGcacccTTTCCGACGCACCGATC
GCAGGTTCGG-3'

SA.neco.D5A4
(SEQ ID NO: 56)
5'-tcggTTTGGGTGGGAGGGTCGGGcacccTTTCCGACGCACCGAT
CGCAGGTTCGG-3'

SA.neco.D5A5
(SEQ ID NO: 57)
5'-tcggTTTGGGTGGGAGGGTCGGGcacccTTTCCGACGCACCGAT
CGCAGGTTCGG-3'

SA.neco.D6A2
(SEQ ID NO: 58)
5'-ggTTTGGGTGGGAGGGTCGGGccacccTTTCCGACGCACCGATC
GCAGGTTCGG-3'

The nucleic acid element (II') is a single-stranded nucleic acid element having a positional relationship in which the binding nucleic acid molecule (A) is interchanged with the catalyst nucleic acid molecule (D), the stem-forming sequence (S_A) is interchanged with the stem-forming sequence (S_D), and the loop-forming sequence (L1) is interchanged with the loop-forming sequence (L2) in the nucleic acid element (II). The nucleic acid element (II') can be described with reference to the description of the nucleic acid element (II) unless otherwise particularly described.

As mentioned above, the nucleic acid element (II') includes a catalyst nucleic acid molecule (D), a loop-forming sequence (L2), a stem-forming sequence (S_A), a binding nucleic acid molecule (A), a loop-forming sequence (L1), and a stem-forming sequence (S_D) linked in this order. A terminal region of the catalyst nucleic acid molecule (D) on the loop-forming sequence (L2) side is complementary to the stem-forming sequence (S_D), and a terminal region of the binding nucleic acid molecule (A) on the loop-forming sequence (L1) side is complementary to the stem-forming sequence (S_A).

In the nucleic acid element (II'), in the absence of SA, the catalytic function of the catalyst nucleic acid molecule (D) is inhibited by stem formation in each of the stem-forming sequences (S_A) and (S_D). The inhibition of the catalytic function occurs by caging the catalyst nucleic acid molecule through such stem formation caused by self-association. That is, by the stem formation, the catalyst nucleic acid molecule (D) cannot have an original structure with which the catalytic function is exerted, thereby inhibiting the catalytic function. On the other hand, in the presence of SA, the stem formation in each of the stem-forming sequences ($S_A$) and ($S_D$) is released by a binding of the SA with the binding nucleic acid molecule (A), and the catalytic function of the catalyst nucleic acid molecule (D) is exerted. The exertion of the catalytic function occurs by releasing the stem formation caused by the self-association and the caging of the catalyst nucleic acid molecule, for example. That is, by releasing the stem formation, the catalyst nucleic acid molecule (D) has an original structure with which the catalytic function is exerted, thereby exerting the catalytic function. Note here that the present invention is not limited by these mechanisms.

As in the nucleic acid element (II), in the nucleic acid element (II'), in the absence of SA, the catalytic function of the catalyst nucleic acid molecule (D) is inhibited (switched OFF) by the stem formation, and in the presence of SA, the catalytic function of the catalyst nucleic acid molecule (D) is exerted (switched ON) by releasing the stem formation. Specifically, in the nucleic acid element (II'), for example, in the absence of SA, a terminal region of the binding nucleic acid molecule (A) on the loop-forming sequence (L1) side and the stem-forming sequence ($S_A$) form a stem, a terminal region of the catalyst nucleic acid molecule (D) on the loop-forming sequence (L2) side and the stem-forming sequence ($S_D$) form a stem, and the loop-forming sequences (L1) and (L2) form an internal loop between the two stems.

Figure 3:
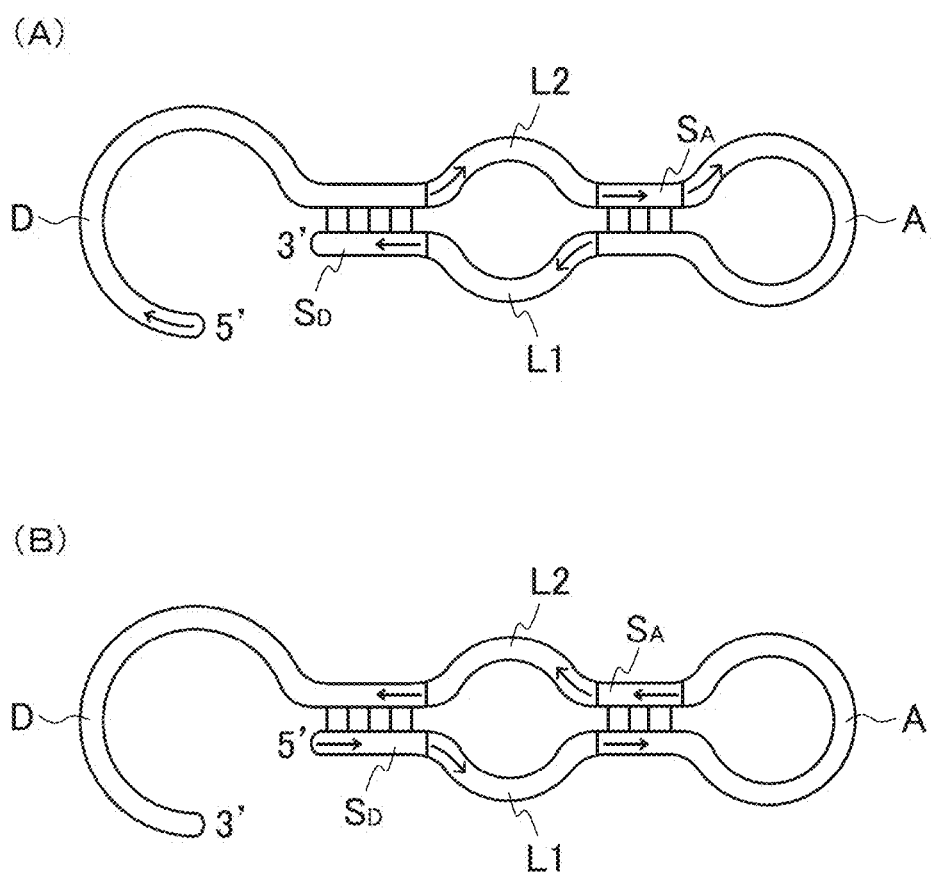
FIGS. 3A and 3B are schematic views showing yet another example of a nucleic acid element in the nucleic acid sensor of the present invention.

The schematic views of FIGS. 3A and 3B show the state of the nucleic acid element (II') in the absence of SA. The form shown in FIG. 3A and the form shown in FIG. 3B are reversed from each other in terms of the direction.

In each of FIGS. 3A and 3B, A represents the binding nucleic acid molecule (A), L1 represents the loop-forming sequence (L1), D represents the catalyst nucleic acid molecule (D), L2 represents the loop-forming sequence (L2), $S_A$ represents the stem-forming sequence ($S_A$), and $S_D$ represents the stem-forming sequence ($S_D$). As shown in each of FIGS. 3A and 3B, in the absence of SA, two stems are formed at the respective two positions by self-annealing of the nucleic acid element (II'), and an internal loop is formed between the stems. Specifically, a stem is formed between a terminal region of the binding nucleic acid molecule (A) on the loop-forming sequence (L1) side, a stem is formed between a terminal region of the catalyst nucleic acid molecule (D) on the loop-forming sequence (L2) side and the stem-forming sequence ($S_D$), and an internal loop is formed between the loop-forming sequences (L1) and (L2). In the presence of SA, the formation of the two stems is released by a binding of SA to the binding nucleic acid molecule (A), thereby exerting catalytic activity of the catalyst nucleic acid molecule (D).

The order of each component in the nucleic acid element (II') is not particularly limited. As shown in FIG. 3B, it is preferred that the nucleic acid element (II') includes, from the 3' side thereof, the catalyst nucleic acid molecule (D), the loop-forming sequence (L2), the stem-forming sequence ($S_A$), the binding nucleic acid molecule (A), the loop-forming sequence (L1), and the stem-forming sequence ($S_D$) linked in this order, for example. In this case, it is preferred that a 5' terminal region of the binding nucleic acid molecule (A) is complementary to the stem-forming sequence ($S_A$), and a 5' terminal region of the catalyst nucleic acid molecule (D) is complementary to the stem-forming sequence ($S_D$).

As shown in FIG. 3A, the nucleic acid element (II') may include, from the 5' side thereof, the catalyst nucleic acid molecule (D), the loop-forming sequence (L2), the stem-forming sequence ($S_A$), the binding nucleic acid molecule (A), the loop-forming sequence (L1), and the stem-forming sequence ($S_D$) linked in this order, for example. In this case, it is preferred that a 3' terminal region of the binding nucleic acid molecule (A) is complementary to the stem-forming sequence ($S_A$), and a 3' terminal region of the catalyst nucleic acid molecule (D) is complementary to the stem-forming sequence ($S_D$).

The nucleic acid element (III) is, as mentioned above, a single-stranded nucleic acid element and includes a catalyst nucleic acid molecule (D), an intervening sequence (I), and a binding nucleic acid molecule (A) linked in this order. The intervening sequence (I) is non-complementary to the catalyst nucleic acid molecule (D) and the binding nucleic acid molecule (A). In the absence of SA, the catalytic function of the catalyst nucleic acid molecule (D) is inhibited. On the other hand, in the presence of SA, the catalytic function of the catalyst nucleic acid molecule (D) is exerted.

As in the nucleic acid elements (I), (II), and (II'), in the nucleic acid element (III), in the absence of SA, the catalytic function of the catalyst nucleic acid molecule (D) is inhibited (switched OFF), and in the presence of SA, the catalytic function of the catalyst nucleic acid molecule (D) is exerted (switched ON).

Figure 4:
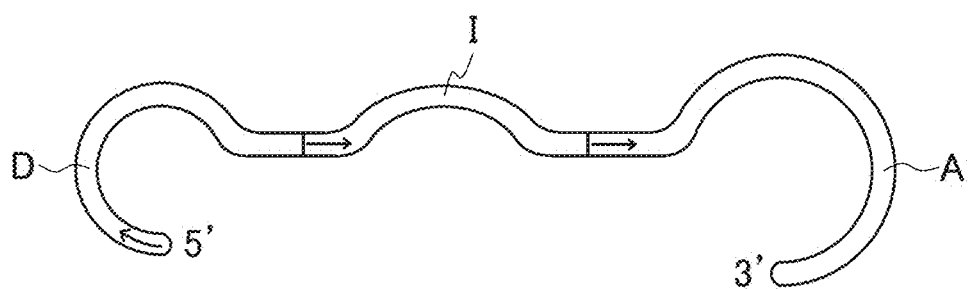
FIGS. 4A and 4B are schematic views showing yet another example of a nucleic acid element in the nucleic acid sensor of the present invention.
Figure 4:
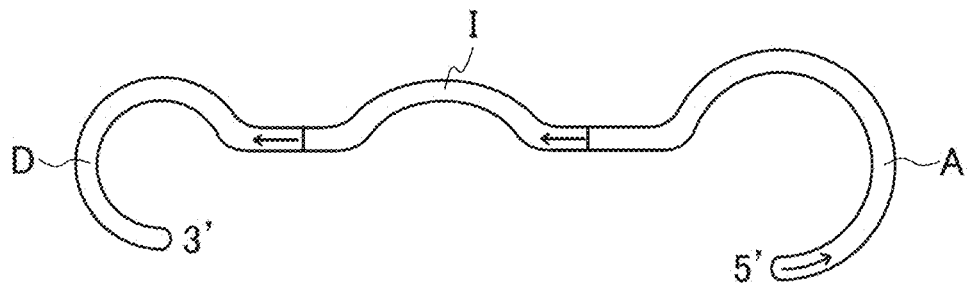

The schematic views of FIGS. 4A and 4B show the state of the nucleic acid element (III) in the absence of SA. In each of FIGS. 4A and 4B, A represents the binding nucleic acid molecule (A), I represents the intervening sequence (I), and D represents the catalyst nucleic acid molecule (D). The form shown in FIG. 4A and the form shown in FIG. 4B are reversed from each other in terms of the direction.

The reason why, in the nucleic acid element (III), the catalytic function of the catalyst nucleic acid molecule (D) is inhibited in the absence of SA and is exerted in the presence of SA can be assumed as follows, for example. The present invention, however, is not limited by the assumption. In the nucleic acid element (III), in the absence of SA, a part of the catalyst nucleic acid molecule (D) and a part of the binding nucleic acid molecule (A) interact with each other, and the catalyst nucleic acid molecule (D) forms non-G quartet. In the presence of SA, the main form of the nucleic acid element (III) becomes close to the original structure of the binding nucleic acid element (A), i.e., a three-dimensional structure with which the binding nucleic acid element (A) binds to SA, and the entire structure changes. Thus, the catalyst nucleic acid molecule (D) forms G-quartet, and the catalytic function is exerted.

The order of each component in the nucleic acid element (III) is not particularly limited. As shown in FIG. 4A, it is preferred that the nucleic acid element (III) includes, from the 5' side thereof, the catalyst nucleic acid molecule (D), the intervening sequence (I), and the binding nucleic acid molecule (A) linked in this order, for example. As shown in FIG. 4B, the nucleic acid element (III) includes, from the 3' side thereof, the catalyst nucleic acid molecule (D), the intervening sequence (I), and the binding nucleic acid molecule (A) linked in this order, for example.

In the nucleic acid element (III), the length of the intervening sequence (I) is not particularly limited. The length of the intervening sequence (I) is, for example, from 0- to 30-mer, from 1- to 30-mer, preferably from 0- to 10-mer, from 1- to 10-mer, more preferably from 0- to 8-mer, from 1- to 8-mer.

The length of the nucleic acid element (III) is not particularly limited. The length of the nucleic acid element (III) is, for example, from 30- to 120-mer, preferably from 35- to 80-mer, more preferably from 40- to 60-mer.

Specific examples of the nucleic acid element (III) are shown below. The present invention, however, is not limited thereby. In the following SA.EAD2.D0.A0, the underlined portion on the 5' side indicates DNAzyme (D in FIG. 4A) of SEQ ID NO: 11 (EAD2), the underlined portion on the 3' side indicates an SA aptamer (A in FIGS. 4A and 4B) of SEQ ID NO: 5, and the poly dT positioned between the DNAzyme and the SA aptamer is an intervening sequence (I in FIG. 4A). In the following SA.neco.D0.A0, the underlined portion on the 5' side indicates DNAzyme (D in FIG. 4A) of SEQ ID NO: 18 (neco0584), the underlined portion on the 3' side indicates an SA aptamer (A in FIG. 4A) of SEQ ID NO: 5, and the poly dT positioned between the DNAzyme and the SA aptamer indicates an intervening sequence (I of FIG. 4A).

```
SA.EAD2.D0.A0
                                        (SEQ ID NO: 59)
5'-CTGGGAGGGAGGGAGGGATTTTTTCCGACGCACCGATCGCAGG
TTCGG-3'

SA.neco.D0.A0
                                        (SEQ ID NO: 60)
5'-GGGTGGGAGGGTCGGGTTTTTTCCGACGCACCGATCGCAGGTT
CGG-3'
```

In each of the nucleic acid elements (I), (II), (II'), and (III), the regions may be directly or indirectly linked, for example. In the case of the direct linking, for example, the regions are linked by a phosphodiester bond. In the case of the indirect linking, for example, the regions are linked via an intervening linker. The intervening linker can be, for example, a nucleic acid molecule composed of the above-mentioned nucleotide and/or non-nucleotide. The intervening linker is, for example, preferably a single strand.

The nucleic acid sensor of the present invention may be, for example, a sensor composed of only the nucleic acid element or a sensor further including any other component(s). The nucleic acid sensor of the present invention can also be referred to as a device for detecting SA, for example. One of the other component(s) can be, for example, a base material on/in which the nucleic acid element is arranged. The base material can be, for example, a base plate, a bead, a container such as a tube, or the like. In addition, one of the other component(s) can be, for example, a linker. The linker can be used to link between the nucleic acid element and the base material when the nucleic acid element is immobilized on the base material, for example. The arrangement of the nucleic acid sensor on the base material can be performed with reference to the description of the analysis device of the present invention described below.

In the nucleic acid element, the linking site with the linker is not particularly limited and is, for example, preferably either one of the terminals of the nucleic acid element. In the double-stranded nucleic acid element (I), the linking site is, for example, preferably either one of the terminals of the first strand (ss1) including the binding nucleic acid molecule (A) and the catalyst nucleic acid molecule (D) and/or either one of the terminals of the second strand (ss2). In each of the single-stranded nucleic acid elements (II), (II'), and (III), the linking site is, for example, preferably either one of the terminals. In this case, the linker is also referred to as a terminal linker. The linker can be, for example, a nucleic acid molecule composed of the above-mentioned nucleotide and/or non-nucleotide. The terminal linker is, for example, preferably a single strand.

The nucleic acid sensor of the present invention may be used in the state where the nucleic acid element is freed or in the state where the nuclei acid element is immobilized, for example. In the latter case, for example, the nucleic acid element is immobilized on the base material, which can be used as a device.

A method for using the nucleic acid sensor of the present invention is not particularly limited and can be used in the method for analyzing SA of the present invention as described below.

The analysis method of the present invention is, as mentioned above, a method for analyzing SA, including: a contact step of causing a sample containing SA to be in contact with the nucleic acid sensor according to the present invention; and a detection step of detecting the catalytic function of the catalyst nucleic acid molecule (D) in the nucleic acid sensor to detect SA in the sample.

The sample is not particularly limited. The sample may be, for example, either one of a sample containing SA and a sample in which whether or not it contains SA is unknown. The sample is, for example, preferably a liquid sample.

When the nucleic acid element in the state of being freed is used as the nucleic acid sensor of the present invention, it is preferred that the nucleic acid element and the sample are caused to be in contact with each other in a container such as a tube, for example. When the nucleic acid element in the state of being arranged on the base material is used as the nucleic acid sensor of the present invention, the sample can be caused to be in contact with the nucleic acid element on the base material, for example.

It is preferred that a signal generated by the catalytic function of the catalyst nucleic acid molecule (D) is detected in the detection step, for example. Examples of the signal include an optical signal and an electrochemical signal. Examples of the optical signal include a chromogenic signal, a luminescent signal, and a fluorescent signal.

It is preferred that the signal is generated from a substrate by the catalytic function of the catalyst nucleic acid molecule (D), for example. Thus, it is preferred that the detection step can be performed in the presence of a substrate appropriate to the catalytic function of the catalyst nucleic acid molecule (D), for example.

The substrate can be, for example, a substrate that generates a chromogenic, luminescent, or fluorescent product by the catalytic function or is a chromogenic, luminescent, or fluorescent substrate and generates a product that quenches its developed color, luminescence, or fluorescence by the catalytic function or generates a different chromogenic, luminescent, or fluorescent product by the catalytic function. According to such substrate, for example, the catalytic function can be detected by observing, as a signal, the presence or absence of developed color, luminescence, or fluorescence or the change in or the intensity of developed color, luminescence, or fluorescence by visual check. Alternatively, for example, the catalytic function can be detected by measuring, as a signal, absorbance, reflectance, or fluorescence intensity using an optical method. The catalytic function can be, for example, the above-mentioned catalytic function of the oxidation-reduction reaction.

In the case where the catalyst nucleic acid molecule (D) has the catalytic function of the oxidation-reduction reaction, the substrate can be, for example, a substrate that can perform electron transfer. In this case, for example, a product is generated from the substrate by the catalyst nucleic acid molecule (D), and in the course of the generation, electrons are transferred. This electron transfer can be electrochemically detected as an electrical signal by applying a voltage to an electrode, for example. The electrical signal can be detected by measuring the intensity of the electrical signal such as a current, for example.

The substrate is not particularly limited, and examples thereof include hydrogen peroxide, 3,3',5,5'-Tetramethylbenzidine (TMB), 1,2-Phenylenediamine (OPD), 2,2'-Azinobis(3-ethylbenzothiazoline-6-sulfonic Acid Ammonium Salt (ABTS), 3,3'-Diaminobenzidine (DAB), 3,3'-Diaminobenzidine Tetrahydrochloride Hydrate (DAB4HCl), 3-Amino-9-ethylcarbazole (AEC), 4-Chloro-1-naphthol (4C1N), 2,4,6-Tribromo-3-hydroxybenzoic Acid, 2,4-Dichlorophenol, 4-Aminoantipyrine, 4-Aminoantipyrine Hydrochloride, and luminol In the detection step, the substrate may be, for example, supplied to the nucleic acid sensor before, at the same time as, or after causing the sample to be in contact with the nucleic acid sensor. It is preferred that the substrate is supplied to the nucleic acid sensor as a substrate liquid obtained by mixing the substrate in a liquid, for example. The liquid in which the substrate is mixed is, for example, preferably a buffer solution such as Tris-HCl. The concentration of the substrate in the substrate liquid is not particularly limited and is, for example, from 0.1 to 5 μmol/L, preferably from 0.5 to 2 μmol/L. The pH of the substrate liquid is, for example, from 6 to 9, preferably from 6.8 to 9.

In the detection step, the conditions of the reaction by the catalyst nucleic acid molecule (D) is not particularly limited. The temperature is, for example, from 15° C. to 37° C., and the time is, for example, from 10 to 900 seconds.

In the detection step, porphyrin may be present together in addition to the substrate, for example. There is known DNAzyme that exerts high oxidation-reduction activity by forming a complex with porphyrin, for example. Thus, in the present invention, for example, a complex between the catalyst nucleic acid molecule (D) and porphyrin may be formed by causing porphyrin to be present together to detect oxidation-reduction activity. The supply of porphyrin is not particularly limited and can be performed in the same manner as for the substrate.

The porphyrin is not particularly limited, and examples thereof include unsubstituted porphyrin and a derivative thereof. Examples of the derivative include substituted porphyrin and a metal porphyrin obtained by forming a complex between porphyrin and a metal element. The substituted porphyrin can be, for example, N-methylmesoporphyrin. The metal porphyrin can be, for example, hemin that is a ferric complex. The porphyrin is, for example, preferably the metal porphyrin, more preferably hemin.

According to the nucleic acid sensor of the present invention, SA can be detected as mentioned above. Moreover, according to the nucleic acid sensor of the present invention, for example, biotin can be indirectly detected, and as a specific example, the binding biotinylated target concentration or the binding biotin concentration can be indirectly detected. In this case, for example, an SA aptamer that binds to a biotin binding site is used as the binding nucleic acid molecule. The SA aptamer and the biotin bind to the same site of SA. Thus, when biotin binds to SA, the SA aptamer cannot bind thereto. Therefore, according to an increase in the amount of biotin, a binding of the SA aptamer with SA is inhibited. Thus, the amount of biotin or biotynated target can be evaluated by causing the nucleic acid sensor of the present invention and SA to react with the biotin or the biotynated target and detecting a catalytic function of the catalyst nucleic acid molecule in the nucleic acid sensor of the present invention.

(Analysis Device and Analysis Method Using the Same)

The analysis device of the present invention is a device for analyzing SA, including: a base material; a nucleic acid sensor; and a detection part, wherein the nucleic acid sensor and the detection part are arranged in the base material, the nucleic acid sensor is the nucleic acid sensor according to the present invention, and the detection part is a detection part that detects the catalytic function of the catalyst nucleic acid molecule (D) in the nucleic acid sensor.

The analysis device of the present invention is characterized in that the nucleic acid sensor of the present invention is used, and the other configurations are not at all limited. The analysis device of the present invention can be described with reference to, for example, the description of the nucleic acid sensor of the present invention unless otherwise specifically described.

A method for arranging the nucleic acid sensor in the analysis device of the present invention is not particularly limited, and the nucleic acid element in the nucleic acid sensor may or may not be immobilized on the base material, for example. In the former case, the nucleic acid element may be directly or indirectly immobilized on the base material, for example. As the immobilization, a linkage by a chemical bond can be shown as an example. The indirect immobilization can have a form of immobilizing the nucleic acid element on the base material via a linker, for example. The linker can be, for example, the above-mentioned terminal linker. The arrangement of the nucleic acid element can be described with reference to the description of the nucleic acid sensor of the present invention, for example.

As the immobilization of the nucleic acid element, a known nucleic acid immobilization method can be employed other than the above-mentioned method, for example. The known nucleic acid immobilization method can be, for example, a method utilizing photolithography, and as a specific example, U.S. Pat. No. 5,424,186 can be used as a reference. The nucleic acid immobilization method can be, for example, a method in which the nucleic acid element is synthesized on the base material. This method can be, for example, a so-called spot method, and as a specific example, U.S. Pat. No. 5,807,522 or JP H10-503841 A can be used as a reference.

A site of the base material on which the nucleic acid element is arranged is not particularly limited and can have, for example, a form of arranging the nucleic acid element in the detection part.

The analysis device of the present invention may further include a regent part, for example. The reagent part may be arranged in the detection part, for example. A reagent may be arranged in the reagent part in advance, or a reagent may be supplied in the reagent part when used. Examples of the reagent include the above-mentioned substrate and porphyrin.

In the analysis device of the present invention, the detection part is, as mentioned above, a detection part that detects the catalytic function of the catalyst nucleic acid molecule (D). The detection part is preferably a detection part that detects, as the catalytic function of the catalyst nucleic acid molecule (D), a signal generated by the catalytic function of the catalyst nucleic acid molecule (D). The signal can be, for example, as mentioned above, a signal generated from the substrate by the catalytic function of the catalyst nucleic acid molecule (D). The signal can be, for example, the above-mentioned optical signal or electrochemical signal.

In the case where the signal is an optical signal, the detection part is, for example, a detection part that detects an optical signal, and the detection part that detects an optical signal can be, for example, a detection part that detects absorbance, reflectance, fluorescence, or the like.

In the case where the signal is the electrochemical signal, the detection part includes an electrode system, for example. In this case, the detection part can be formed by arranging the electrode system on the surface of the base material, for example. A method for arranging the electrode is not particularly limited, and a known method can be employed, for example. Specific examples thereof include methods for forming a thin film such as a vapor deposition method, a sputtering method, a screen printing method, and a plating method. The electrode may be arranged directly or indirectly on the base material. The indirect arrangement can be, for example, an arrangement via another member.

The electrode system may be an electrode system including a working electrode and a counter electrode or an electrode system including a working electrode, a counter electrode, and a reference electrode, for example. The material of each electrode is not particularly limited, and examples thereof include platinum, silver, gold, and carbon. Examples of the working electrode and the counter electrode include a platinum electrode, a silver electrode, a gold electrode, and a carbon electrode. The reference electrode can be, for example, a silver/silver chloride electrode. The silver-silver chloride electrode can be formed by laminating a silver chloride electrode on a silver electrode, for example.

In the case where the analysis device of the present invention has the electrode system, the nucleic acid element is preferably arranged in the electrode system, more preferably arranged in the working electrode among the electrodes. In the case where the analysis device of the present invention includes the electrode system and the reagent part, the reagent part is preferably arranged on the electrode system, for example.

The analysis device of the present invention may include plural detection parts, for example. In this case, for example, in the analysis device, it is preferred that the surface of the base material is fractionated into matrix, and each fraction region is provided with each of the above-mentioned detection parts. In the analysis device of the present invention, the number of nucleic acid sensors arranged in one detection part is not particularly limited.

The base material is not particularly limited. The base material is, for example, preferably a base material having an insulating surface. The base material may be a base plate composed of an insulating material or a base material having, on the surface thereof, an insulating layer composed of an insulating material. The insulating material is not particularly limited, and examples thereof include known materials such as glass, ceramics, an insulating plastic, and paper. The insulating plastic is not particularly limited, and examples thereof include a silicone resin, a polyimide resin, an epoxy resin, and a fluorine resin.

The analysis method of the present invention is, as mentioned above, a method for analyzing SA, including: a contact step of causing a sample to be in contact with the analysis device according to the present invention; and a detection step of detecting the catalytic function of the catalyst nucleic acid molecule (D) in the detection part of the analysis device to detect SA in the sample.

The analysis method of the present intention is characterized in that the analysis device including the nucleic acid sensor of the present invention is used, and the other conditions are not at all limited. The analysis method of the present invention can be described with reference to the description of the analysis method in the description of the nucleic acid sensor of the present invention, for example.

(Analysis Reagent)

The analysis reagent of the present invention contains the nucleic acid sensor of the present invention. The analysis reagent of the present invention is characterized in that it contains the nucleic acid sensor, and the other configurations are not at all limited.

The analysis reagent of the present invention may further contain, in addition to the nucleic acid sensor, a component(s) such as the substrate, the porphyrin, the buffer solution, and/or the base material, for example.

The analysis reagent of the present invention may be, for example, an analysis kit. In this case, for example, the analysis kit may contain the nucleic acid sensor and the above-mentioned component(s), and they may be contained individually. The analysis kit may further contain the instruction manuals thereof, for example.

EXAMPLES

Example 1

A single-stranded nucleic acid element (III) including an SA aptamer as a binding nucleic acid molecule (A) and EAD2 as a catalyst nucleic acid molecule (D) was produced, and the performance thereof as a nucleic acid sensor was checked.

As the nucleic acid element, DNA having the following sequence was synthesized (see FIG. 4A). In the sequence, the underlined portion on the 5' side indicates the EAD2 (D) of SEQ ID NO: 11, the underlined portion on the 3' side indicates an SA aptamer (A) of SEQ ID NO: 5, and the poly dT positioned between the EAD2 (D) and the SA aptamer (A) indicates an intervening sequence (I).

```
SA.EAD2.D0.A0
                                      (SEQ ID NO: 59)
5'-CTGGGAGGGAGGGAGGGATTTTTTCCGACGCACCGATCGCAGG
TTCGG-3'
```

In Eppendorf tubes, 100 µL each of the respective reaction solutions having the following composition containing SA with the predetermined concentrations (0, 2, 5, 10, 15, and 20 µmol/L) were prepared and then caused to react for 5 minutes at 25° C. Thereafter, color development of each reaction solution was observed by visual check. Subsequently, the absorbance (wavelength: 415 nm) of the reaction solution after 2 minutes from the initiation of the reaction was measured. As a substrate, ABTS (2,2'-Azinobis (3-ethylbenzothiazoline-6-sulfonic Acid Ammonium Salt) was used.

(Composition of Reaction Solution)

| Nucleic acid sensor | 2 µmol/L |
|---|---|
| Substrate | 1 mmol/L |
| Hemin | 3 µmol/L |
| SA | Predetermined concentration |

In parallel, as a positive control, a reaction solution (PC) using EAD2 of SEQ ID NO: 11 as a substitute for the nucleic acid sensor was subjected to the same reaction as described above. Moreover, as a negative control 1 (NC), a reaction was performed in the same manner as mentioned above except that an SA aptamer of SEQ ID NO: 5 was used as a substitute for the nucleic acid sensor, and as a negative control 2, a reaction solution (W/O) containing no nucleic acid sensor was subjected to the same reaction.

```
EAD2
                                              (SEQ ID NO: 11)
CTGGGAGGGAGGGAGGGA

SA aptamer
                                              (SEQ ID NO: 5)
CCGACGCACCGATCGCAGGTTCGG
```

Figure 5:
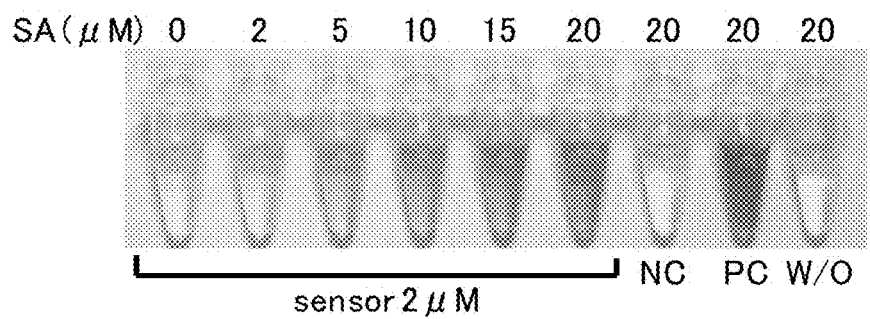
FIG. 5A is a photograph of reaction solutions in Example 1.
FIG. 5B is a graph showing measurement results of absorbance in Example 1.
Figure 5:
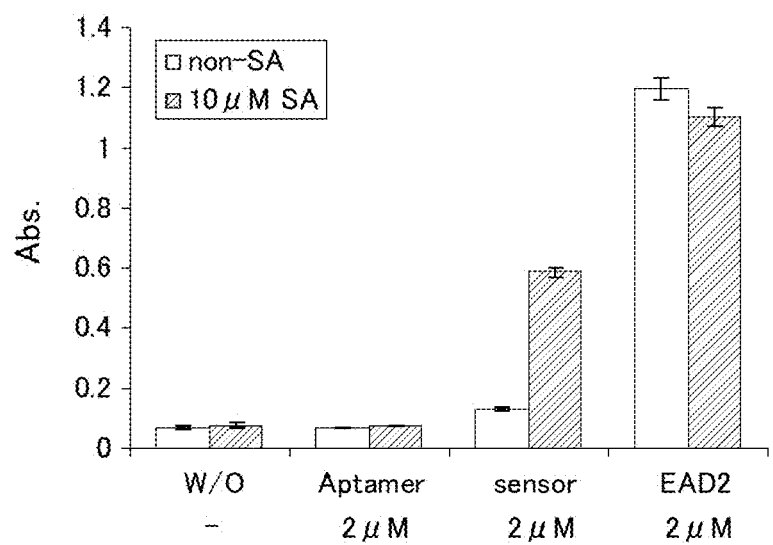

These results are shown in FIGS. 5A and 5B. FIGS. 5A and 5B show results of color development of the respective reaction solutions. FIG. 5A is a photograph showing coloring of each reaction solution, and the deeper the color is, the more intense the color development of blue is. FIG. 5B is a graph showing absorbance of each of the reaction solutions with the concentrations of SA of 0 and 10 µmol/L.

As shown in FIG. 5A, in the result in the case of using the nucleic acid sensor of Example 1, the color development became intense as an increase in concentration of SA. Accordingly, it is demonstrated that the coloring of the reaction solution depends on the concentration of SA. Therefore, it can be said that, according to the nucleic acid sensor of Example 1, the presence or absence of and the concentration of SA can be determined by visual check.

Moreover, as shown in FIG. 5B, in the result in the case of using the nucleic acid sensor of Example 1, it was determined that the absorbance was increased as an increase in concentration of SA. Therefore, it can be said that, according to the nucleic acid sensor of Example 1, the presence or absence of and the concentration of SA can be measured by measuring the absorbance.

Example 2

A single-stranded nucleic acid element (II) including an SA aptamer as a binding nucleic acid molecule (A) and DNAzyme as a catalyst nucleic acid molecule (D) was produced, and the performance thereof as a nucleic acid sensor was checked.

As the nucleic acid elements, DNAs having the following respective sequences were synthesized (see FIG. 2B). In each of the sequences, from the 5' side thereof, the sequence indicated by lower-case letters indicates a stem-forming sequence ($S_A$), the poly dT indicated by capital letters indicates a loop-forming sequence (L2), the underlined portion indicates DNAzyme (D) of SEQ ID NO: 18 (neco0584), the sequence indicated by lower-case letters indicates a stem-forming sequence ($S_D$), the poly dT indicated by capital letters indicates a loop-forming sequence (L1), and the under lined portion indicates an SA aptamer (A) of SEQ ID NO: 5.

```
SA.neco.D3A2
                                              (SEQ ID NO: 46)
5'-ggTTTGGGTGGGAGGGTCGGGcccTTTCCGACGCACCGATCGC
AGGTTCGG-3'

SA.neco.D3A3
                                              (SEQ ID NO: 47)
5'-cggTTTGGGTGGGAGGGTCGGGcccTTTCCGACGCACCGATCG
CAGGTTCGG-3'

SA.neco.D3A4
                                              (SEQ ID NO: 48)
5'-tcggTTTGGGTGGGAGGGTCGGGcccTTTCCGACGCACCGATC
GCAGGTTCGG-3'

SA.neco.D3A5
                                              (SEQ ID NO: 49)
5'-gtcggTTTGGGTGGGAGGGTCGGGcccTTTCCGACGCACCGAT
CGCAGGTTCGG-3'

SA.neco.D4A2
                                              (SEQ ID NO: 50)
5'-ggTTTGGGTGGGAGGGTCGGGacccTTTCCGACGCACCGATCG
CAGGTTCGG-3'

SA.neco.D4A4
                                              (SEQ ID NO: 52)
5'-tcggTTTGGGTGGGAGGGTCGGGacccTTTCCGACGCACCGAT
CGCAGGTTCGG-3'

SA.neco.D5A2
                                              (SEQ ID NO: 54)
5'-ggTTTGGGTGGGAGGGTCGGGcacccTTTCCGACGCACCGATC
GCAGGTTCGG-3'

SA.neco.D6A2
                                              (SEQ ID NO: 58)
5'-ggTTTGGGTGGGAGGGTCGGGccacccTTTCCGACGCACCGAT
CGCAGGTTCGG-3'
```

In Eppendorf tubes, 100 µL each of the respective reaction solutions having the following composition was prepared and then caused to react for 60 seconds at 25° C. Thereafter, the absorbance (wavelength: 415 nm) of each reaction solution was measured. In the measurement, an absorbance measurement device (trade name: TECAN infinite, manufactured by TECAN) was used. In the reaction solution, the composition of the DNAzyme buffer contains 50 µmol/L Tris-HCl (pH7.4), 20 µmol/L KCl, and 0.05% TritonX-100. As a substrate, ABTS (2,2'-Azinobis(3-ethylbenzothiazoline-6-sulfonic Acid Ammonium Salt) was used.

(Composition of Reaction Solution)

| | |
|---|---|
| 1 µmol/L | Nucleic acid sensor |
| 3 µmol/L | Hemin |
| 1 µmol/L | SA |
| 1 mmol/L | Substrate |
| 0.5 mmol/L | $H_2O_2$ |
| | 1x DNAzyme buffer |

In parallel, as a positive control, DNAzyme of SEQ ID NO: 18 (neco0584) was used as a substitute for the nucleic acid sensor. Moreover, as a negative control, a reaction solution (W/O) containing no nucleic acid sensor was subjected to the same reaction as described above.

```
neco0584
                                              (SEQ ID NO: 18)
GGGTGGGAGGGTCGGG
```

Figure 6:
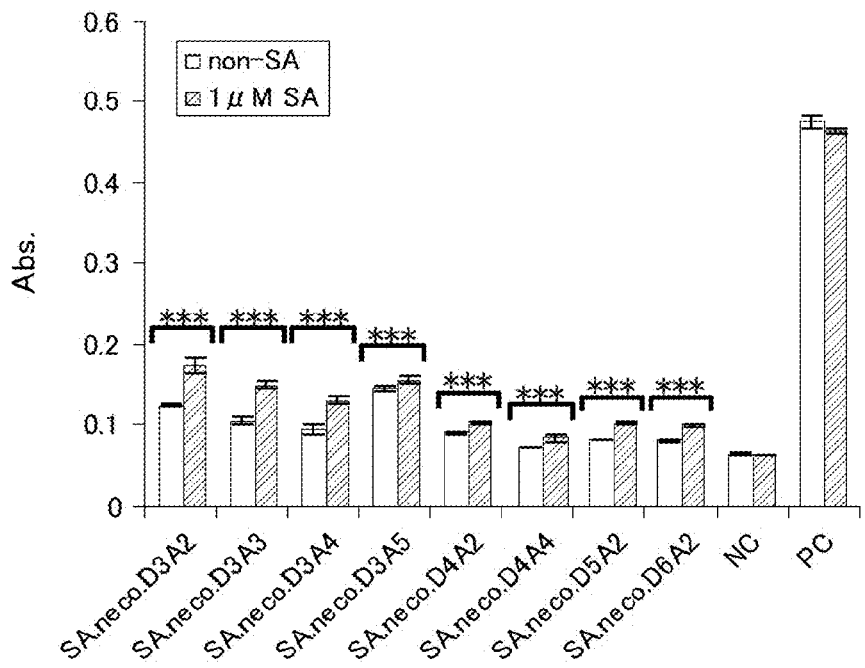
FIG. 6 is a graph showing measurement results of absorbance in Example 2.

These results are shown in FIG. 6. FIG. 6 is a graph showing absorbance of each of the reaction solutions. As shown in FIG. 6, in the result in the case of using the nucleic acid sensor of Example 2, the absorbance of the reaction solution containing 1 µmol/L SA showed a significant difference to the absorbance of the reaction solution containing no SA. As can be seen from this result, it can be said that, according to the nucleic acid sensor of Example 2, the presence or absence of and the concentration of SA can be measured by measuring absorbance, and specifically, SA can be detected even in the case of 1 µmol/L SA.

Example 3

A double-stranded nucleic acid element (I) including an SA aptamer as a binding nucleic acid molecule (A) and DNAzyme as a catalyst nucleic acid molecule (D) was produced, and the performance thereof as a nucleic acid sensor was checked.

As a first strand (ss1), DNA having the following sequence was synthesized (see FIG. 1A). In the following sequence, the underlined portion on the 5' side indicates an SA aptamer (A), the poly dT indicates a loop-forming sequence (L1), and the underlined portion on the 3' side indicates DNAzyme (D) of SEQ ID NO: 18 (neco0584).

```
SA.neco.D3A2
                                        (SEQ ID NO: 32)
5'-CCGACGCACCGATCGCAGGTTCGGTTTTTTTTGGGTGGGAGGG
TCGGG-3'
```

As a second strand (ss2) to be paired with the first strand (ss1), DNA having the following sequence was synthesized (see FIG. 1A). In the following sequence, the underlined portion on the 5' side indicates a stem-forming sequence ($S_D$) complementary to a 5' side region of the DNAzyme of the first strand (ss1), the poly dT indicates a loop-forming sequence (L2), and the underlined portion on the 3' side indicates a stem-forming sequence ($S_A$) complementary to a 3' side region of an SA aptamer of the first strand (ss1).

```
        SA.neco.D8.A5
                                        (SEQ ID NO: 45)
        5'-TCCCACCCTTTTTTTTCCGAA-3'
```

In Eppendorf tubes, 100 µL each of the respective reaction solutions having the following composition was prepared and then caused to react for 60 seconds at 25° C. Thereafter, the absorbance (wavelength: 415 nm) of each reaction solution was measured. In the measurement, an absorbance measurement device (trade name: TECAN infinite, manufactured by TECAN) was used. In the reaction solution, the composition of the DNAzyme buffer contains 50 µmol/L Tris-HCl (pH7.4), 20 µmol/L KCl, 150 µmol/L, and 0.05% TritonX-100. As a substrate, ABTS was used.

(Composition of Reaction Solution)

| | |
|---|---|
| 1 µmol/L | First strand (ss1) |
| 2 µmol/L | Second strand (ss2) |
| 3 µmol/L | Hemin |
| 1 µmol/L | SA |
| 50 mmol/L | DNAzyme buffer |
| 1 mmol/L | Substrate |
| 0.5 mmol/L | H$_2$O$_2$ |

In parallel, as a positive control (PC), a reaction solution using DNAzyme of SEQ ID NO: 18 (neco0584) as a substitute for the nucleic acid sensor was subjected to the same reaction as described above. Moreover, as a negative control (NC), a reaction solution containing no nucleic acid sensor was subjected to the same reaction as described above. Furthermore, a reaction solution containing only the first strand (ss1) without containing the second strand (ss2) was subjected to the same reaction as described above.

```
            neco0584
                                        (SEQ ID NO: 18)
            GGGTGGGAGGGTCGGG
```

Figure 7:
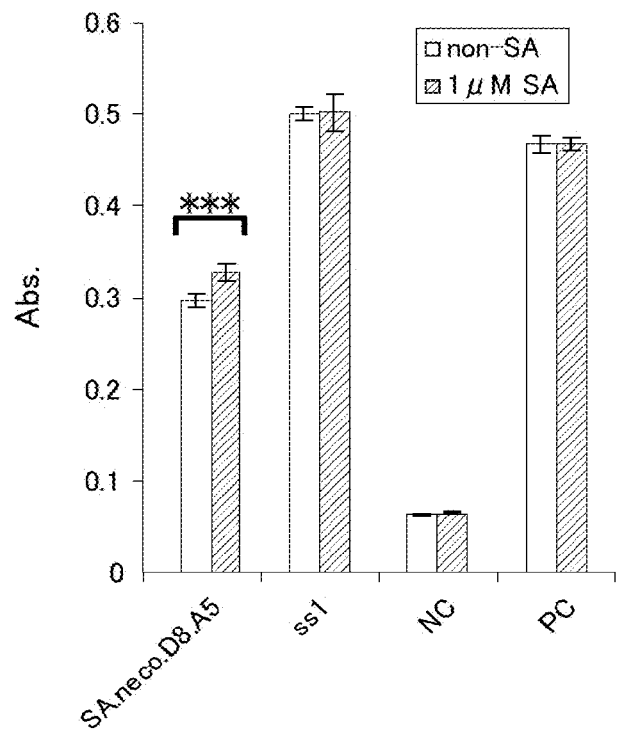
FIG. 7 is a graph showing measurement results of absorbance in Example 3.

These results are shown in FIG. 7. FIG. 7 is a graph showing absorbance of each of the reaction solutions. As shown in FIG. 7, in the result in the case of using the nucleic acid sensor of Example 3, the absorbance of the reaction solution containing 1 µmol/L SA showed a significant difference to the absorbance of the reaction solution containing no SA. As can be seen from this result, it can be said that, according to the nucleic acid sensor of Example 2, the presence or absence of and the concentration of SA can be measured by measuring absorbance, and specifically, SA can be detected even in the case of 1 µmol/L SA.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

This application is based upon and claims the benefit of priority from Japanese patent application No. 2012-067947, filed on Mar. 23, 2012, the disclosure of which is incorporated herein its entirety by reference.

INDUSTRIAL APPLICABILITY

According to the present invention, the catalytic function of the catalyst nucleic acid molecule (D) can be switched ON/OFF by a binding/non-binding of the binding nucleic acid molecule (A) with SA. Therefore, the presence or absence of and the amount of SA can be easily detected by detecting the catalytic function of the catalyst nucleic acid molecule. Moreover, the analysis device of the present invention uses the nucleic acid sensor as mentioned above. Therefore, for example, the analysis device can be downsized and formed into a chip, and many specimens can be easily analyzed by the analysis device. Thus, it can be said that the present invention is a really useful technology for researches and inspections in various fields such as clinical medical care, food, and environment, for example.

The invention claimed is:

1. A nucleic acid sensor for analyzing streptavidin, comprising
a nucleic acid element (II) that comprises a single-stranded nucleic acid element comprising a binding nucleic acid molecule (A) that binds to streptavidin, a loop-forming sequence (L1), a stem-forming sequence ($S_D$), a catalyst nucleic acid molecule (D) that exerts a redox function, a loop-forming sequence (L2), and a stem-forming sequence ($S_A$) linked in this order, wherein
a terminal region of the binding nucleic acid molecule (A) on the loop-forming sequence (L1) side is complementary to the stem-forming sequence ($S_A$),
a terminal region of the catalyst nucleic acid molecule (D) on the loop-forming sequence (L2) side is complementary to the stem-forming sequence ($S_D$),
the loop-forming sequence (L1) is non-complementary to the loop-forming sequence (L2), and
wherein, in the absence of streptavidin,
the redox function of the catalyst nucleic acid molecule (D) is inhibited by stem formation in each of the stem-forming sequences ($S_A$) and ($S_D$), and
in the presence of streptavidin,
the stem formation in each of the stem-forming sequences ($S_A$) and ($S_D$) is released by a binding of the streptavidin with the binding nucleic acid molecule (A), and the redox function of the catalyst nucleic acid molecule (D) is exerted,
a terminal region of the binding nucleic acid molecule (A) on the loop-forming sequence (L1) side and the stem-forming sequence ($S_A$) form a stem,
a terminal region of the catalyst nucleic acid molecule (D) on the loop-forming sequence (L2) side and the stem-forming sequence ($S_D$) form a stem, and
the loop-forming sequences (L1) and (L2) form an internal loop between the two stems.

2. The nucleic acid sensor according to claim 1, wherein the nucleic acid element (II) comprises, from the 3' side thereof, the binding nucleic acid molecule (A), the loop-forming sequence (L1), the stem-forming sequence ($S_D$), the catalyst nucleic acid molecule (D), the loop-forming sequence (L2), and the stem-forming sequence ($S_A$) linked in this order,
a 5' terminal region of the binding nucleic acid molecule (A) is complementary to the stem-forming sequence ($S_A$), and
a 5' terminal region of the catalyst nucleic acid molecule (D) is complementary to the stem-forming sequence ($S_D$).

3. The nucleic acid sensor according to claim 1, wherein the length of each of the loop-forming sequences (L1) and (L2) ranges from 1- to 30-nucleotides.

4. The nucleic acid sensor according to claim 2, wherein the length of the stem-forming sequence ($S_A$) ranges from 1- to 60-nucleotides, and
the length of the stem-forming sequence ($S_D$) ranges from 1- to 30-nucleotides.

5. The nucleic acid sensor according to claim 1, wherein the length of the binding nucleic acid molecule (A) ranges from 18- to 85-nucleotides.

6. The nucleic acid sensor according to claim 1, wherein the binding nucleic acid molecule (A) comprises the following polynucleotide (a1), (a2), (a3), or (a4):
(a1) a polynucleotide composed of a base sequence of any of SEQ ID NOs: 1 to 10,
(a2) a polynucleotide that is composed of a base sequence obtained by substitution, deletion, addition and/or insertion of at least one base in the base sequence of the polynucleotide (a1) and binds to streptavidin,
(a3) a polynucleotide that is composed of a base sequence with 50% or more identity with the base sequence of the polynucleotide (a1) and is bindable to streptavidin, and
(a4) a polynucleotide that is composed of a base sequence complementary to a base sequence that hybridizes to the base sequence of the polynucleotide (a1) under stringent conditions and is bindable to streptavidin.

7. The nucleic acid sensor according to claim 1, wherein the catalytic function of the catalyst nucleic acid molecule (D) is the catalytic function of an oxidation-reduction reaction.

8. The nucleic acid sensor according to claim 1, wherein the length of the catalyst nucleic acid molecule (D) ranges from 15- to 30-nucleotides.

9. The nucleic acid sensor according to claim 1, wherein the catalyst nucleic acid molecule (D) comprises the following polynucleotide (d1), (d2), (d3), or (d4):
(d1) a polynucleotide composed of a base sequence of any of SEQ ID NOs: 11 to 31 and 61 to 80,
(d2) a polynucleotide that is composed of a base sequence obtained by substitution, deletion, addition, and/or insertion of at least one base in the base sequence of the polynucleotide (d1) and exerts a catalytic function of an oxidation-reduction reaction,
(d3) a polynucleotide that is composed of a base sequence with 50% or more identity with the base sequence of the polynucleotide (d1) and exerts a catalytic function of an oxidation-reduction reaction, and
(d4) a polynucleotide that is composed of a base sequence complementary to a base sequence that hybridizes to the base sequence of the polynucleotide (d1) under stringent conditions and exerts a catalytic function of an oxidation-reduction reaction.

10. A device for analyzing streptavidin, comprising:
a base material;
a nucleic acid sensor; and
a detection part, wherein
the nucleic acid sensor and the detection part are disposed on the base material,
the nucleic acid sensor is the nucleic acid sensor according to claim 1, and
the detection part is a detection part that detects the catalytic function of the catalyst nucleic acid molecule (D) in the nucleic acid sensor.

11. The device according to claim 10, wherein the nucleic acid sensor is linked with the base material via a linker.

12. The device according to claim 10, wherein the nucleic acid sensor is disposed on the detection part.

13. The device according to claim 10, wherein the detection part detects a signal generated by the catalytic function of the catalyst nucleic acid molecule (D).

14. The device according to claim 13, wherein the signal is an optical signal or an electrochemical signal.

15. The device according to claim 10, further comprising:
a reagent part, wherein the reagent part comprises a substrate to the catalytic function of the catalyst nucleic acid molecule (D).

16. A method for analyzing streptavidin, comprising:
a contact step of causing a sample to be in contact with the nucleic acid sensor according to claim 1; and
a detection step of detecting the catalytic function of the catalyst nucleic acid molecule (D) in the nucleic acid sensor to detect streptavidin in the sample.

17. The method according to claim 16, wherein the detection step is performed in the presence of a substrate to the catalytic function of the catalyst nucleic acid molecule (D).

18. A method for analyzing streptavidin, comprising:
a contact step of causing a sample to be in contact with the device according to claim 10; and
a detection step of detecting the catalytic function of the catalyst nucleic acid molecule (D) in the detection part of the device to detect streptavidin in the sample.

19. The method according to claim 18, wherein the detection step is performed in the presence of a substrate to the catalytic function of the catalyst nucleic acid molecule (D).

* * * * *